(12) United States Patent
Whitehouse et al.

(10) Patent No.: US 7,232,992 B2
(45) Date of Patent: Jun. 19, 2007

(54) CHARGED DROPLET SPRAYERS

(75) Inventors: Craig M. Whitehouse, Branford, CT (US); Thomas White, Branford, CT (US)

(73) Assignee: Analytica of Branford, Inc., Branford, CT (US)

( * ) Notice: Subject to any disclaimer, the term of this patent is extended or adjusted under 35 U.S.C. 154(b) by 0 days.

(21) Appl. No.: 11/132,953

(22) Filed: May 19, 2005

(65) Prior Publication Data
US 2005/0258360 A1 Nov. 24, 2005

Related U.S. Application Data

(60) Provisional application No. 60/573,666, filed on May 21, 2004.

(51) Int. Cl.
*B01D 59/44* (2006.01)
*G01N 24/00* (2006.01)

(52) U.S. Cl. .................. 250/288; 436/173; 436/140

(58) Field of Classification Search ............... 250/288, 250/281, 282; 204/451; 436/173, 140
See application file for complete search history.

(56) References Cited

U.S. PATENT DOCUMENTS

| | | | | |
|---|---|---|---|---|
| 5,306,412 A | * | 4/1994 | Whitehouse et al. | 204/452 |
| 5,393,975 A | * | 2/1995 | Hail et al. | 250/288 |
| 5,879,949 A | * | 3/1999 | Cole et al. | 436/173 |
| 5,917,184 A | * | 6/1999 | Carson et al. | 250/288 |
| 6,252,225 B1 | * | 6/2001 | Takada et al. | 250/288 |
| 6,326,616 B1 | * | 12/2001 | Andrien et al. | 250/288 |
| 6,437,327 B2 | * | 8/2002 | Takada et al. | 250/288 |
| 6,630,664 B1 | * | 10/2003 | Syage et al. | 250/288 |
| 6,784,439 B2 | * | 8/2004 | Van Berkel | 250/423 R |
| 6,858,841 B2 | * | 2/2005 | Truche et al. | 250/288 |
| 2003/0209005 A1 | * | 11/2003 | Fenn | 60/203.1 |
| 2006/0022130 A1 | * | 2/2006 | Bousse et al. | 250/288 |

* cited by examiner

*Primary Examiner*—Nikita Wells
*Assistant Examiner*—Johnnie L Smith, II
(74) *Attorney, Agent, or Firm*—Levisohn Berger LLP

(57) ABSTRACT

Charged droplet spray is formed from a solution with all or a portion of the charged droplet spray current generated from reduction or oxidation (redox) reactions occurring on surfaces removed from the first or sample solution flow path. In one embodiment of the invention, two solution flow channels are separated by a semipermeable membrane. A first or sample solution flowing through the first solution flow channel exchanges cation or anion charged species through the semipermeable membrane with a second solution or gas flowing through the second flow channel. Charge exchange is driven by the electric field applied at the charged droplet sprayer sample solution outlet. Redox reactions occur at an electrode surface in contact with the second solution. The invention increases the control and range of the Electrospray ionization process during ES/MS operation. Alternative embodiments of the invention provide for conducting redox reactions on conductive surfaces removed from the first or sample solution flow path but not separated by semipermeable membranes.

16 Claims, 22 Drawing Sheets

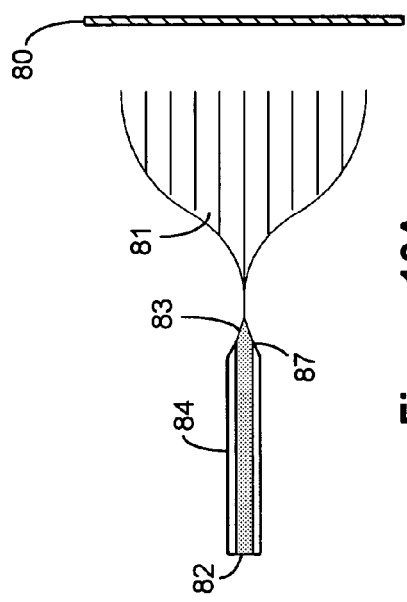
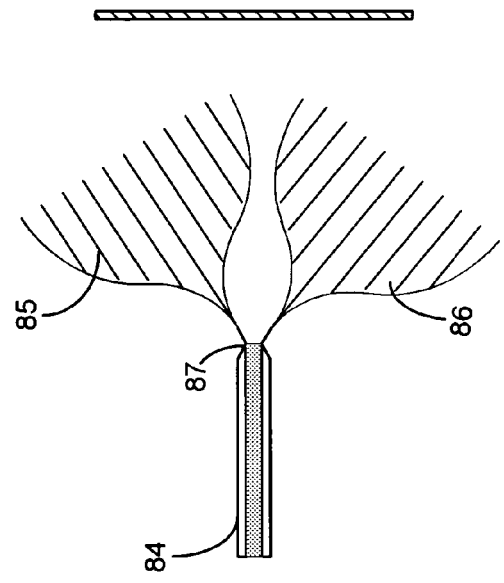
Figure 10A
Figure 10B

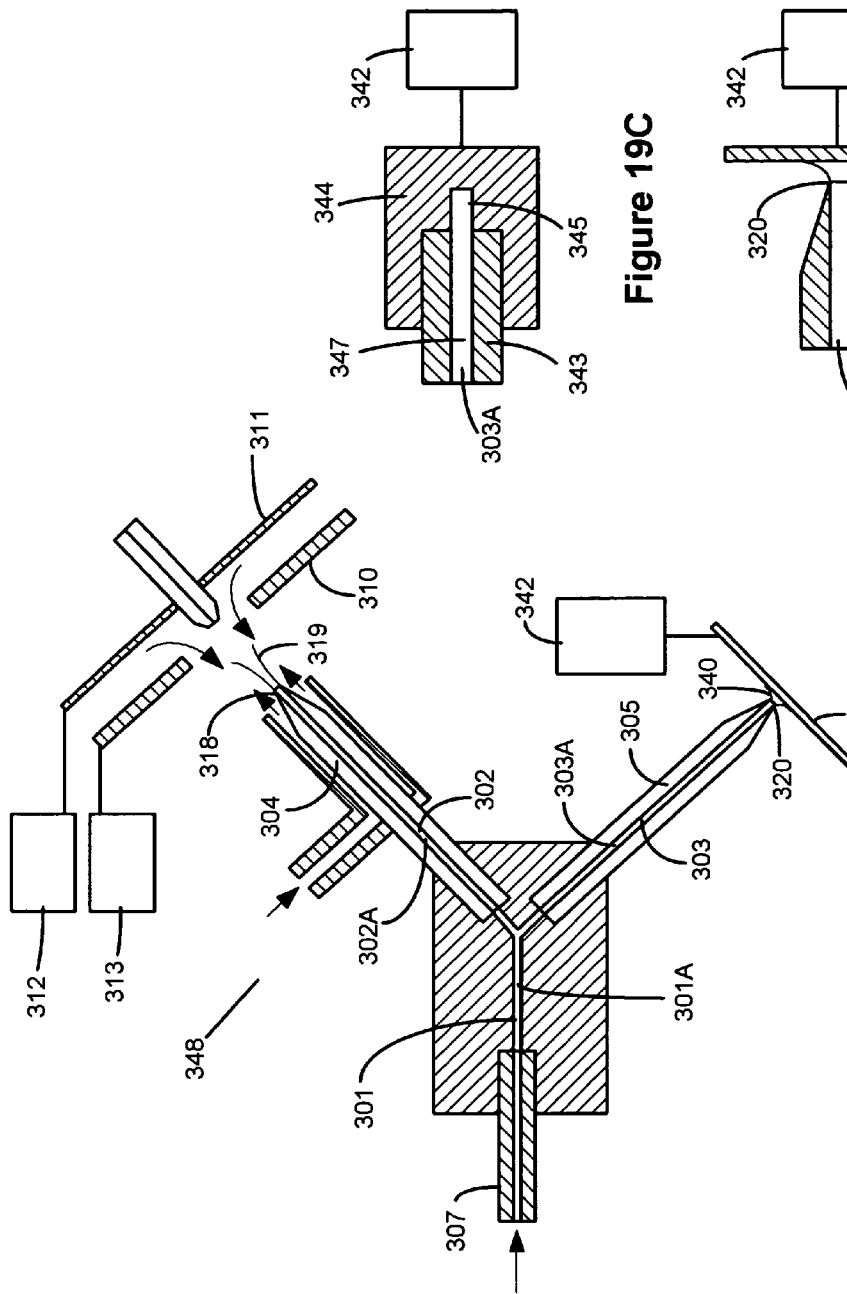
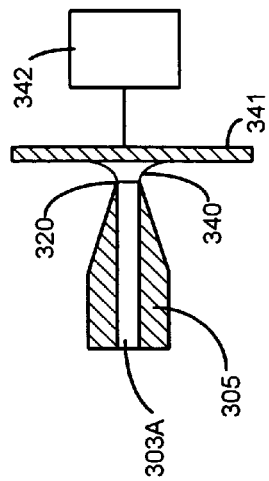
Figure 19C
Figure 19B
Figure 19A

CHARGED DROPLET SPRAYERS

CROSS-REFERENCE TO RELATED APPLICATION

This application claims priority to U.S. Provisional Application No. 60/573,666, filed on May 21, 2004, the disclosure of which is incorporated herein by reference in its entirety.

FIELD OF THE INVENTION

The invention relates to the production of charged liquid droplet sprays generated in Electrospray ionization sources interfaced to mass spectrometers.

BACKGROUND OF THE INVENTION

Sprays of charged liquid droplets can be produced through Electrospray and pneumatic nebulization or ultrasonic nebulization in the presence of an electric field. The mechanisms of ion production from unassisted Electrospray ionization have been described by Karbarle, P., J. Mass Spectrom. 35, 804-817 (2000)[1], and Karbarle, P. and Ho, Y. "Electrospray Ionization Mass Spectrometry", Edited by Richard Cole, Chapter 1, 3-63, 1997[2]. The oxidation and reduction chemical reactions that occur, or that can be induced to occur, on conductive surfaces located in sample solution flow channels prior to or during the charged droplet formation process in Electrospray have been described by Van Berkel, G. L. "Electrospray Ionization Mass Spectrometry", Edited by Richard Cole, Chapter 2, 65-105, 1997[3], Van Berkel, G. J., J. Am. Soc. Mass Spectrom. 2000, 11, 951-960[4] and Van Berkel, G. J., Asano, K. G. and Kertesz, V., Anal. Chem. 2002, 74, 5047-5056[5]. Promotion of oxidation or reduction of sample species on conductive surfaces during Electrospray ionization followed by mass spectrometric analysis can be a useful tool to enhance the sensitivity or aid in determining the structure of specific sample species. The production of ion species in sample solutions through reduction/oxidation reactions on surfaces in the first solution flow channel with solutions retaining a total net neutral charge prior to Electrospraying for mass spectrometrometric analysis has been reported by Hackett et. al., U.S. Pat. No. 5,869,832[6]. Commercially available products are available from ESA Inc., Chelmsford, Mass., that promote electrochemical reactions on surfaces in the sample solution flow path by applying voltages across electrodes extending into the sample solution flow. Specific electrode materials have been explored to control analyte oxidation in sample solutions prior to Electrospraying [5]. Split flow fractionation techniques used in conjunction with Electrospray ionization have been described by Van Berkel, U.S. Pat. No. 6,677,593 B1 [7] where electric or magnetic fields are applied across a sample solution in a flow path using two electrodes positioned on opposite sides of a sample solution flow path in contact with the solution flow to separate positive and negative ions into separate sample solution flow streams prior to charged droplet spraying. Van Berkel describes charged droplet spraying from such devices even without the presence of an external electric field applied at sample solution channel exit tips. Multiple Electrospray tips have been configured from a single sample solution flow channel by Kostianen and Bruins, Rapid Comm. in MS, Vol. 8, 549-558 (1994)[8]. Simultaneous Electrospraying of a sample solution from positive and negative sprays partitions the sample species in a manner that may not be readily predictable or controlled.

Neutral and charged species have been exchanged across membranes, transferred into and/or removed from sample solution flows to reduce or eliminate selected species in exchange for other selected species in a sample solution prior to Electrospraying. Acid and/or salt concentrations in a sample solution have been reduced by exchange across species specific semipermeable membranes prior to Electrospraying. Charged or neutral species are exchanged between a sample solution and a second solution through a semipermeable membrane driven by concentration gradients or electric fields maintained across such membranes while retaining an electrically neutral sample solution. In such devices electrodes are positioned in the first and second flow channels in contact with the sample solution and the second solution. Charged species in the sample and second solutions are neutralized through redox reactions occurring on the first and second flow channel electrode conductive surfaces resulting in a net neutral sample solution flow exiting these membrane devices. Such devices have been described and are sold by Dionex Corporation. The electric field is maintained across the membrane in these devices by applying a voltage difference between electrodes positioned in the first and second solution flow channels on either side of the membrane. The electric field applied across these electrodes drives the charged species across the membrane between the sample solution and second solutions. The electric field applied across the membrane in these devices is configured upstream and operated independent of a second electric field formed in the Electrospray process if these devices are interfaced to an Electrospray ion source through a connecting flow tube. The charged droplet spray current produced in these devices interfaced to an Electrospray probe is generated from redox reactions occurring at conductive surfaces located in the sample solution flow channel.

The present invention eliminates the occurrence of oxidation or reduction reactions on conductive surfaces in the sample solution flow channel during Electrospray Ionization (ES) while providing control of the total Electrospray current generated during the charged droplet formation process. The total Electrospray current has a direct impact on the size distribution of the charged droplets produced. In one embodiment of the invention, a sample solution flow channel is separated from a second solution or gas phase flow channel by a semipermeable membrane. The solution or gas composition flowing through the second flow channel can be varied as a step function or gradient during Electrospraying. In charged droplet sprayer embodiments configured according to the invention, the Electrospray field present at the sample solution spray tip during Electrospray is the only electric field driving charged species formation in the sample solution and second solution flow channels. Van Berkel, et. al. [5] describe the use of a cellulose ester 5000 Da molecular mass cutoff membrane membrane covering an electrode surface to prevent redox reactions of sample molecules on the electrode surface during the Electrospraying. The electrode is maintained at a kilovolt potential during Electrospraying, with an upstream grounded electrode positioned the sample solution flow path. No second solution is used behind the membrane in the reported Electrospray apparatus and no current measurement was taken on the grounded conductive surface in the sample flow path during Electrospray ionization to determine the extent of redox reactions occurring at the grounded electrode surface in the sample solution flow path. No explanation is given by the authors as to how the electrical contact is completed between the sample solution and the electrode through the membrane but it is likely that the sample solution wetting the membrane forms the electrical contact with the electrode maintained at kilovolt potentials during Electrospray ionization.

Severs, J. C., Harms, A. C., and Smith, R. D., Rapid Communications in Mass Spectrometry, Vol. 10, 1175-1178 (1996) and Severs, J. C. [9] and Smith, R. D., Anal. Chem. 1997, 69, 2154-2158 [10] describe a capillary electrophoresis (CE) Electrospray interface with a mass spectrometer (MS) in which a polysulfone dialysis membrane with a molecular weight cutoff of 10,000 Da separates the capillary electrophoresis solution from a second electrolyte solution in contact with a CE column exit electrode. In the CE/ES/MS interface described, the total Electrospray current is a small fraction of the total CE current flowing to the CE column exit electrode surface. In the CE runs reported, a +30 kV potential was maintained at the CE column entrance. In positive ion mode CE/ES operation reported, reduction occurs at the CE column exit electrode maintained at +1.6 kV as electrons pass from the electrode into the second electrolyte solution. During this CE/ES operation described, net positive charge transfers from the CE column solution into the second electrolyte solution through the membrane during positive Electrospray ionization. The net positive charge for charged droplet production in Electrospray appears to be supplied by a small portion of the electrophoretic charge moving from entrance to exit through the CE column driven by the 30 kV electrical potential applied at the CE column entrance. In the CE/ES apparatus described, the electric field maintained across the dialysis membrane is in the opposite direction required to supply charge for positive polarity Electrospray ionization. As described by Severs et. al. [9, 10] the second solution with electrolyte added is a static solution volume placed in a capillary tube surrounding the CE column exit end. The capillary tube has open ends to allow release of gas formed in redox reactions at the CE column exit electrode surface. The second electrolyte solution appears to remain in place due to surface tension of the liquid in the capillary tube. The authors report changing the second solution between CE/ES/MS runs, replacing the ammonium acetate solution with an acetic acid solution, resulting in a shift in charge state of multiply charged peaks appearing in mass spectrum of myoglobin and carbonic anhydrase. The shifting of the multiply charged profile to increased charge state peaks would occur with a reduction of pH in the CE solution. How this apparent decrease in pH occurs is not explained by the authors. The electric field applied across the membrane during CE/ES/MS with the apparatus described would have driven positively charged protons from the CE column solution into the second electrolyte solution effectively decreasing pH in the CE solution. One explanation could be that a portion of acetic acid in second solution remains in a neutral form and neutral acetic acid molecules may have transferred through the dialysis membrane into the CE solution driven by a concentration gradient during CE/ES/MS operation.

As described in the prior art, it may be desireable in some analytical applications to cause redox reactions with sample substances in solution prior to Electrospray MS analysis. However, for many applications it is preferable to minimize any changes to the analyte species in solution prior to Electrospraying to achieve minimum distortion of information regarding a solution composition in ES/MS analysis. In many applications including quantitative analysis, the study of peptides and proteins, high throughput screening, drug discovery, drug metabolite studies and biomarker detection it is preferred to have minimum modification of the analyte population during ES/MS analysis. The Electrospray probe apparatus configured according to the invention allows control of the Electrospray current using only the Electrospray electric field while preventing redox reactions from occurring on conductive surfaces in the first or sample solution flow path during Electrospray ionization. One embodiment of the invention provides control of the total Electrospray current and sample solution pH while preventing redox reactions from occurring on conductive surfaces in the sample solution flow path. This control of the Electrospray process allows optimization of ES/MS or ES/MS$^n$ analysis and expansion of ES/MS$^n$ or liquid chromatography Electrospray mass MS (LC/ES/MS$^n$) analytical capability while insuring minimum modification of the analytes in the sample solution due to redox reactions prior to Electrospraying. The introduction of specific neutral or charged species into the sample solution through semipermeable membranes during Electrospray ionization can be selected and controlled to maximize ion signal for different classes of analyte compounds in the sample solution. The invention allows conducting of conductivity or pH scans during Electrospraying to maximize ion signal or to study processes occurring in solution such as protein folding as a function of pH. Preventing redox reactions from occurring on conductive surfaces in the first or sample solution flow path minimizes the carryover of contamination species that deplate from the conductive surfaces when the Electrospray polarity is changed. The contamination ions occurring in mass spectra when polarity is changed can reduce sample signal due to charge competition and cause interference peaks in the acquired mass spectrum. The charged droplet sprayer configured according to the invention reduces the time and solvent consumption required to flush sample solution flow paths, providing increased analytical throughput at lower cost per analysis.

The electrical circuit equivalence of conventional Electrospray ionization charged droplet formation and neutralization processes have been described by Kebarle, P., and Tang, L., Anal. Chem. 1993, 65, 972A-985A [11] and Jackson, G. S., and Enke, C. G., Anal. Chem. 1999, 71, 3777-3784 [12]. The total electrical current generated in unassisted or pneumatic nebulization assisted Electrospray is established by electrolytic processes occurring in solution. For a given voltage differential applied between the Electrospray tip and counter electrodes and for a given liquid flow rate, the total Electrospray current produced through the formation of charged liquid droplets is a strong function of the resistance, or inversely the conductivity, of the solution being Electrosprayed. The invention allows changing of the effective solution conductivity during Electrospraying by changing of the conductivity of a second solution flow separated from the sample solution flow by a semipermeable membrane. Charged species exchanged across the membrane between the first or sample solution and the second solution, effectively changing the conductivity of the sample solution, are driven across the membrane by the applied Electrospray electric field. Selected neutral species may also traverse the membrane driven by a concentration gradient between the first and second solutions that may also change the first solution conductivity. The controlled exchange of proton charged species across the membrane changes the first solution conductivity and pH. The invention allows the addition of protons or cations to the sample solution during positive polarity Electrospray ionization without the addition of the counter ion as is the case when acids or salts are added directly to the sample solution. The converse is true for negative polarity Electrospray ionization.

The total Electrospray current can be changed with precise and stable control during Electrospray ionization with no change to the charged droplet sprayer geometry or the applied Electrospray voltage. For a given solution flow rate, as the total Electrospray current increases, the size of the charged droplets produced decreases. Higher total Electrospray currents with smaller droplet size distributions allows faster drying of charged droplets and the reduction of aerosols produced from evaporating droplets with insufficient charge available to ionize non volatile components within the droplet. In unassisted Electrospray charged droplet production, each initial charged droplet breaks off with approximately half the Rayleigh limit of charge per droplet. For a given liquid flow rate, as the total ES current increases due to increasing solution conductivity, the total number of droplets produced must increase to carry the additional charge limited by the Rayleigh limit of charge per droplet. As the number of charged droplets produced per time increases, the charge to solution volume ratio increases. The same trends apply with pneumatic nebulization assisted Electrospray ionization charged droplet formation. Increasing the total charge available will increase analyte ES/MS$^n$ signal to the point where sufficient charge is available to ionize all analytic molecules. Increasing the total ES current beyond the equivalent analyte concentration may cause a decrease in ES/MS$^n$ signal. The charged droplet sprayer configured according to the invention allows rapid adjustment of total ES current during Electrospray ionization to maximize analyte signal in ES/MS$^n$ analysis.

Embodiments of the invention include charged droplet sprayers configured such that no redox reactions occur on conductive surfaces in the first or sample solution flow path during charged droplet formation in Electrospray ionization. In one embodiment of the invention, charged species are added to or removed from the first or sample solution through semipermeable, dielectric membranes separating the first solution from a second solution or gas flow. In this embodiment, the total charged droplet spray current produced from the charged droplet spraying process can be adjusted by modifying the second solution or gas phase composition, electric field strength across the membrane, electrode composition and geometry, membrane composition and geometry, the electric field at the spray tip, the number of spray tips, solution flow rate and other variables independent of the initial first or sample solution composition as will become apparent in the description of the invention. Through adjustment of such variables using the charged droplet sprayer configured according to the invention, charged droplet spraying can be optimized for a given application. For example, the amplitude of multiply charged peaks of proteins in a mass spectrum acquired by Electrospraying from an aqueous solution can be increased by adding protons through a fluorethylene polymer (Nafion™) dielectric membrane during Electrospraying using one embodiment of the invention. Alternative embodiments of the invention provide for charge separation and the addition or removal of net charge from the first or sample solution with all or a portion of the total charge droplet spray current generated through redox reactions occurring on conductive electrodes separate from the first solution flow path. Embodiments of the invention allow adjustment and optimization of charged droplet spraying for a given sample solution composition.

SUMMARY OF THE INVENTION

The invention comprises embodiments of charged droplet sprayers that provide increased performance and the ability to optimize charged droplet spray performance over a range of operating conditions and applications. In one embodiment of the invention, the charged droplet sprayer comprises a first and a second solution flow channel separated by a single or layered semipermeable dielectric membrane. Selected charged species are transferred into or removed from the first solution through the membrane creating a net increase in one polarity charge in the first solution flow during charged droplet spraying. The first solution, with an increase in one charge polarity, forms a spray of charged droplets at one or more first solution flow channel exit tips. The transfer of charged species through the membrane and the production of the charged droplets from the first solution flow channel exit tip are driven by the Electrospray electric field maintained at the first solution flow channel exit tip. The membrane and the first and second solutions form electrically resistive conduits between the Electrospray electric field present at the first solution flow channel exit tip and an electrode surface positioned in the second solution flow channel in contact with the second solution. The Electrospray electric field maintained at the first solution flow channel exit tip is established by the relative electrical potentials applied to counter electrodes spaced from the exit tip and the electrical potential applied to the electrode in contact with the second solution in the second solution flow channel. The charged species transferred into or removed from the first solution flow through the membrane is determined by selection of the membrane composition, composition of the second solution electrode, composition and flow rates of the first and second solutions and the polarity of the electric field across the membrane. Positive and negative polarity charged droplet spray current can be optimized for a given application by adjusting the variables of solution chemistries and flow rates, relative electrical potentials applied to electrodes and by the selection of membrane materials. Total Electrospray current can be changed during Electrospray ionization by changing the second solution composition and/or first solution flow rate.

Protons can be transferred from the second solution into aqueous sample solutions to increase solution charge and decrease solution pH during positive polarity charged droplet spraying without adding acid species directly to the first solution. Redox reactions occur at conductive electrode surfaces positioned in one or more second solution flow channels driven by the Electrospray electric field. The same electric field drives the charged species across the membrane between the first and second solutions. Deposition of anions on first solution flow channel conductive surfaces is minimized or eliminated during positive ion polarity Electrospray. This avoids deplating of anions from conductive surfaces in the sample solution flow path when the Electrospray ion polarity is reversed. The interference anions produced by deplating from conductive surfaces in negative polarity ES can result in charge suppression of analyte species and the occurrence of unwanted contamination peaks in acquired mass spectra. The converse holds when switching from negative to positive polarity Electrospray ionization. In analytical applications requiring upstream sample separation techniques such as in LC/ES/MS$^n$ analysis, conductive surfaces cannot be entirely eliminated in upstream sample solution flow paths due to the presence of upstream LC columns, valves, fittings and pumps. In such cases, the voltage applied to the electrode in contact with the second solution can be adjusted to minimize or eliminate the occurrence of redox reactions on upstream conductive surfaces in the sample solution flow channel. Embodiments of the invention enable the generation of charged droplet sprays in which the total Electrospray or charged droplet spray current produced is greater than the electrical current generated due to reduction or oxidation reactions occurring on conductive surfaces in the first solution flow channel. In charged droplet sprayers configured according to the invention, redox reactions supplying electrical current to the charged droplet formation process in Electrospray occur on electrode surfaces configured external to the first solution flow channel.

In alternative embodiments of the invention, charged droplet sprayers can be configured with the first solution separated from multiple second solutions by individual membranes comprised of similar or different materials. Different charged species can be individually or simultaneously added to and/or removed from the first solution during charged droplet spraying using multiple membrane embodiments. The first solution flow channel may be configured to terminate with single or multiple exit tips. Generating multiple charged droplet sprays from multiple exit tips allows an increase in the total charged droplet spray current produced for a given first solution composition and allows optimization of the overall charged droplet spray geometry for specific applications. Charged droplet sprays with single or multiple exit tips can be formed using unassisted Electrospray or pneumatic nebulization of solution in the presence of an electric field, alternatively described as Electrospray with pneumatic nebulization assist.

An alternative embodiment of the invention comprises first and second solution flow channels separated by a semipermeable dielectric membrane configured with an insulated porous electrode positioned adjacent to the first solution side of the membrane or configured between membrane layers. The electric field formed between the insulated porous membrane and the electrode configured to be in contact with the second solution in the second solution flow channel can be adjusted to increase or decrease charge species transfer through the membrane. The addition of the insulated porous membrane allows additional control of charged species transfer into or out of the first solution without the need to adjust solution chemistry in the first or second solutions during charged droplet spraying. The charged droplet sprayer can be configured with multiple second solution flow channels separated from the first solution by separate membranes. Conversely, the charged droplet sprayer can be configured with multiple first solution channels separated from a second solution flow channel by separate membranes. The multiple first solution flow channel configuration allows the simultaneous spraying of positive and negative polarity charged droplets from two sprayer exit tips using the same or different first solutions. Alternately, charged droplet sprays of the same polarity may be generated from the two sprayer tips from different first solutions.

An alternative embodiment of the invention comprises a single first solution flow channel configured with two exit tips with only dielectric surfaces or no connected conductive surfaces present in the first solution flow channel where reduction or oxidation (redox) reactions can occur. Opposite polarity charged droplets of the first solution are sprayed simultaneously from the two exit tips toward counter electrodes having different electrical potentials applied. Such dual output, dual polarity charged droplet sprayer may be combined with the membrane separated first and second solution flow channel sprayer embodiment described above to allow addition or removal of one charged species to the first solution through the membrane and bifurcation of charge species in the first solution flow path during charged droplet spraying. Using such combined charged droplet sprayer configuration, the total charged droplet spray current of opposite polarity may not be equal from both tips. Such current balance can be adjusted by selecting the appropriate relative electrical potentials applied to electrodes. One of the two exit tips may be positioned sufficiently close to a counter electrode such that solution leaving the exit tip forms an electrical contact with the counter electrode without spraying. Using this embodiment, separation of charge in the first solution can be achieved during charged droplet spraying while avoiding redox reactions on surfaces in the first solution flow channel and without the need to optimize two charged droplet sprays simultaneously. Finer control of the remaining single charged droplet spray can be achieved by adjusting solution chemistry or applied voltages using such dual outlet embodiment employing solution contact to the counter electrode. Alternatively, such a second solution channel may be terminated with an end electrode allowing electrical contact with the first sample solution removed from the first solution flow path while preventing loss of sample solution flow to the electrode.

In an alternative embodiment of the invention, the first sample solution composition may be modified during charged droplet spraying through a liquid junction configured between a first and second solution flow channel of a dual output opposite polarity charged droplet sprayer embodiment. The geometry of the liquid junction between both solutions can be configured to maximize or minimize contact between the two solutions while allowing exchange of charged species. The dual flow channel charged droplet sprayer embodiment may be configured and operated to prevent flow of the first solution into the second solution flow channel, allow flow of the first solution into the second solution or vice versa, during charged droplet spraying. As described above, to simplify optimization and control of charged droplet spraying from one exit tip, the second flow channel exit tip can be positioned sufficiently close to a counter electrode such that the liquid leaving the exit tip forms an electrical contact with the counter electrode. Charged droplet spray can be generated from the first solution flow channel exit tip using Electrospray or Electrospray with pneumatic nebulization assist. Embodiments of the invention may be combined to allow more flexibility and range in controlling the charged droplet spray process. Increased control of the charged droplet formation process and the sample solution composition during Electrospray ionization allows enhancement and optimization of ES/MS$^n$ and LC/ES/MS$^n$ performance for given applications. Charged droplet spraying can be conducted using the embodiments of the invention or using combinations of embodiments of charged droplet sprayer devices configured according to the invention whereby the charged droplet spray current produced is greater than the electrical current generated due to redox reactions occurring on conductive surfaces in the first solution flow channel.

BRIEF DESCRIPTION OF THE INVENTION

FIG. 10A is a diagram of a charged droplet spray comprising a single stable Electrospray plume.

FIG. 10B is a diagram of a charged droplet spray comprising two stable Electrospray plumes.

FIGS. 19A, B and C are cross section diagram views of a charged droplet sprayer with pneumatic nebulization comprising two outlet channels with one outlet forming a solution contact with an electrode.

Figure 20:
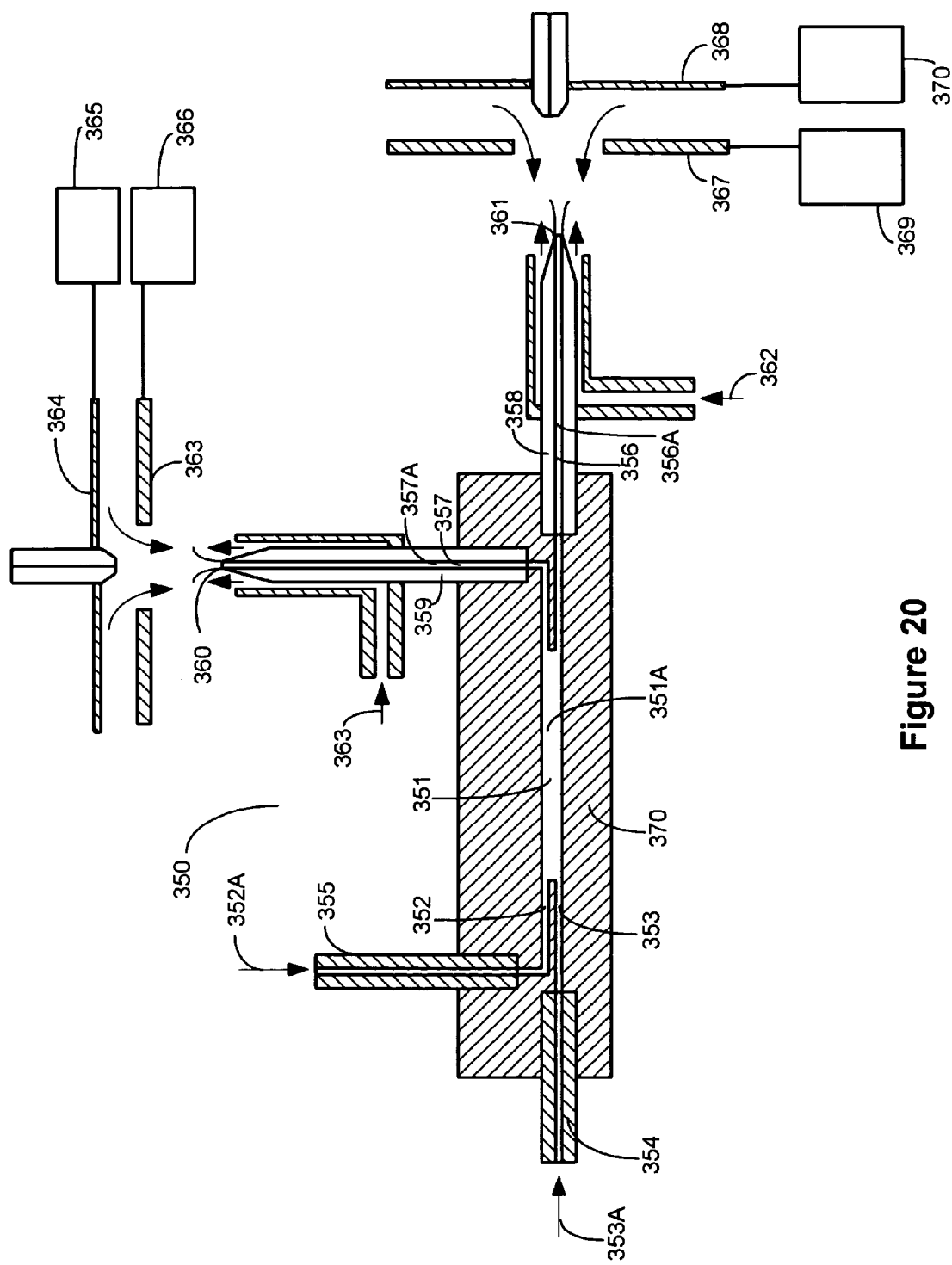

FIG. 20 is a cross section diagram of a charged droplet sprayer comprising two solution inlets into a common flow channel and two sprayer outlets producing charged droplet sprays of opposite polarity.

Figure 21:
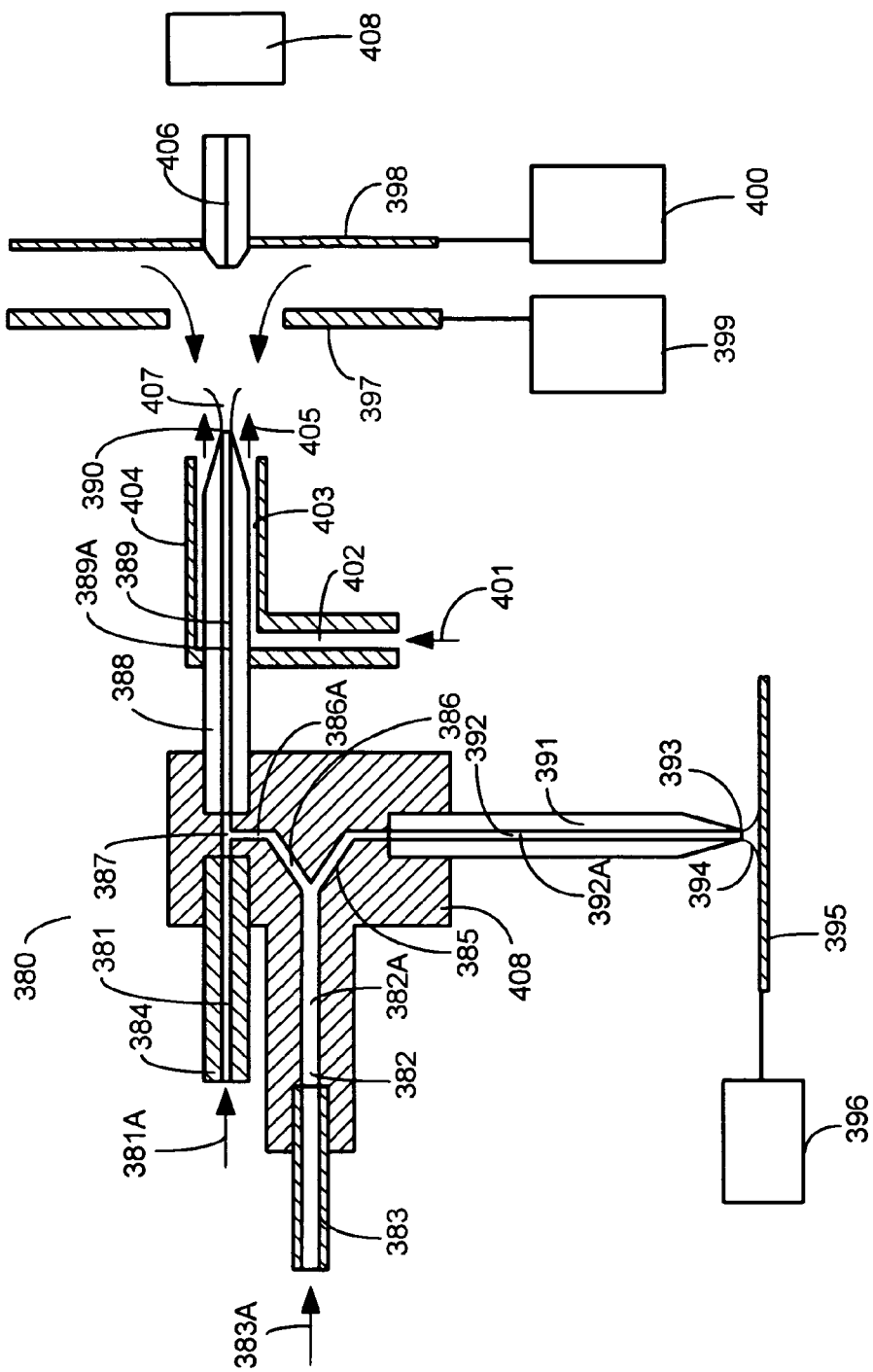

FIG. 21 is a cross section diagram of a charged droplet sprayer comprising separate first and second solution inputs and outputs with a fluid connection between the first and second solution flow channels.

DESCRIPTION OF THE INVENTION

Charged liquid droplets can be formed in charged droplet spray devices using unassisted Electrospray or pneumatic nebulization in the presence of an electric field. Charged droplet production in unassisted Electrospray requires the formation of a stable Taylor cone jet from the sample solution exiting a channel or tube in the presence of an electric field. The charged droplets form by separating from a liquid filament protruding from the tip of the Taylor cone. If a sample solution has high surface tension, it may not be possible to form a stable Taylor cone at atmospheric pressure where electrical potentials applied have an upper limit due to gas phase break down. If the conductivity of a sample solution is too high, the filament projecting from the Taylor cone may not separate into uniform charged droplets due to damping of the fluid column instability by charge movement within the solution. Stable Taylor cones are more difficult to sustain at higher liquid flow rates. Both ultrasonic and pneumatic nebulization charged droplet sprayer devices have been reported and both nebulization techniques can be applied to the embodiments of the invention described below. Pneumatic nebulization sprayer devices are most widely used for the generation of charged liquid droplets from sample solutions. Pneumatic nebulization charged droplet sprays form from a channel or tube tip in the presence of an electric field by pneumatically shearing the solution as it exits the tube. The gas shearing force acting on the exiting liquid stream is sufficient to create charged droplet sprays even for higher surface tension and higher conductivity solutions and for higher liquid flow rate operating conditions. The Taylor cone and liquid filament structure formed in Electrospray to generate charged liquid droplets does not exist in pneumatically nebulized charged droplet sprays. Consequently, charged droplet production using Electrospray (unassisted Electrospray) or pneumatic nebulization in the presence of an electric field (Electrospray with pneumatic nebulization assist) are described in relation the invention as two distinct processes. Both processes achieve the production of charged droplets but each has a different performance response with respect to the invention and each generate different charged droplet size distributions.

Using unassisted Electrospray or pneumatic nebulization in the presence of an electric field to form charge droplet sprays, the charged droplet current generated is a function of the conductivity of the solution, location and material of the conductive surface in the fluid flow path, the location of the reduction-oxidation (redox) reaction in the fluid path, the liquid flow rate, the externally applied electric field strength, the solution composition and the flow channel and flow channel exit tip material and geometry. The charged species or ions formed from evaporating liquid droplets are a function of the sample solution composition, the flow channel conductive material, the total Electrospray current and the droplet drying conditions. The invention provides control of the transfer of known and selected charged species into or out of the sample solution flow channel and provides control of the total charge produced by through the charged droplet spray process with the same initial sample solution composition. In one embodiment of the invention, the reduction-oxidation reactions required for charge separation during charged droplet production occurs in a second gas or solution flow channel separated from the first or sample solution flow channel by a semipermeable dielectric membrane. The total number of charge species transferred through the membrane per time period can be adjusted by modifying the composition of solution or gas flowing through the second channel and the voltage applied to the electrode configured in the second solution flow channel. In another embodiment of the invention, the total charge generated by the charged droplet spray is modified by changing the electrical potentials applied to electrodes positioned within the first and second flow channels. In a third embodiment of the invention, charge separation is achieved in the solution flow channel by splitting the flow into a positive and negative electrically biased channels. The ability to control the transfer of charged species, total charged droplet spray current and the location of the reduction-oxidation reactions, independent of the first solution composition and flow path allows the optimization of Electrospray and nebulization assisted Electrospray charged droplet spray performance in atmospheric pressure ion sources interfaced to mass spectrometers and in other applications. The charged droplet sprayer configured according to the invention allows modification to the Electrospray ionization process using direct user or computer program control.

Figure 1:
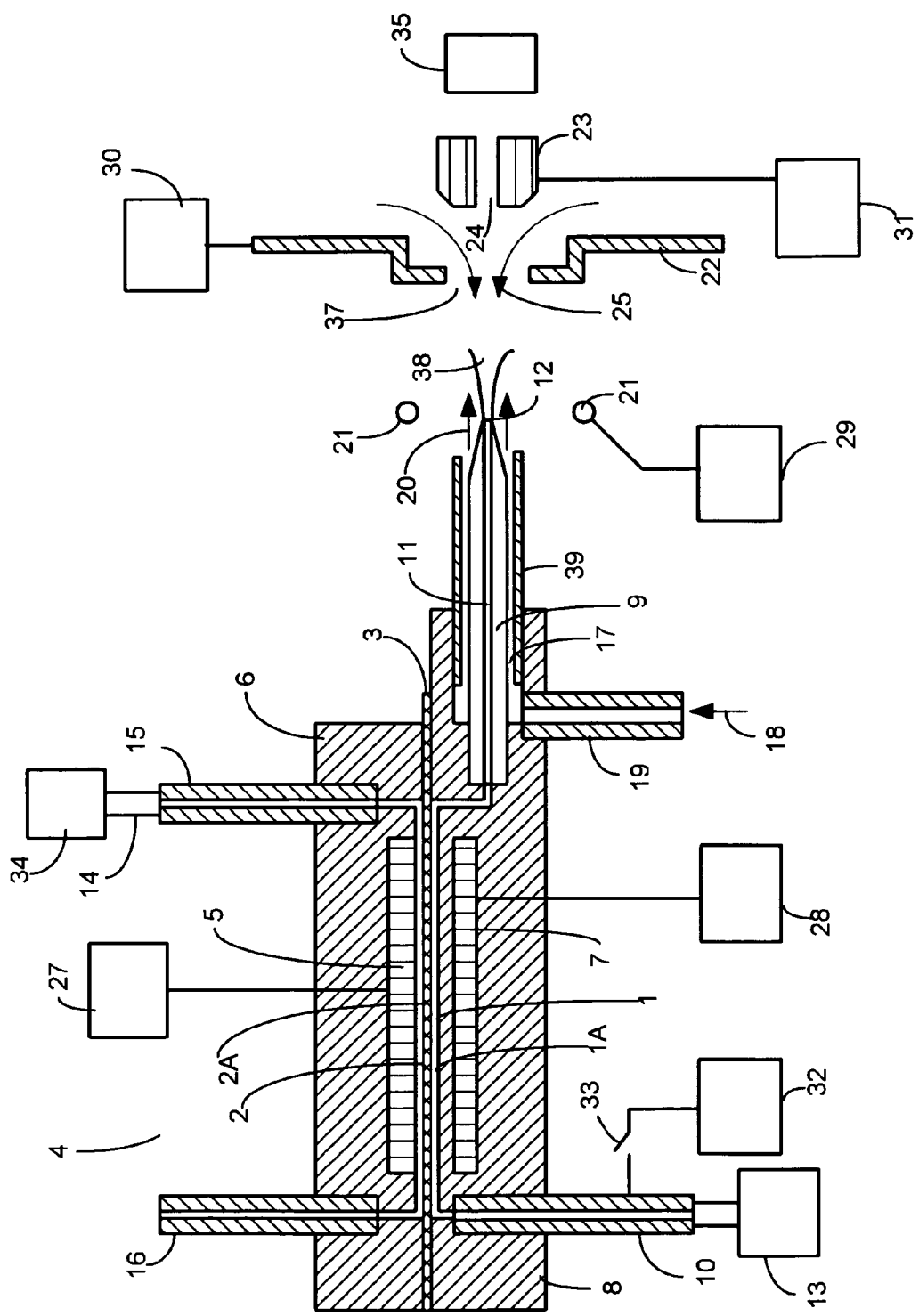
FIG. 1 is a cross section view of single exit tip charged droplet sprayer assembly with pneumatic nebulization comprising first and second solution flow channels separated by a membrane.

FIG. 1 is a cross section diagram of one embodiment of the invention where flow channel 1 and flow channel 2, are separated by membrane 3 in charged droplet sprayer assembly 4. Charged droplet sprayer assembly 4 comprises conductive element or electrode 5 in contact with the liquid or gas flow through channel 2 and dielectric body 8 in contact with the liquid flow through channel 1. Conductive element 5 is mounted in sprayer body 6 comprising dielectric or conductive material. Flow channel 2 is configured for gas or liquid flow through channel 2 of sprayer assembly 4. Dielectric or electrically insulating body 8 is configured with channel 1 to allow flow of sample solution along the surface of membrane 3 with minimum dead volume. Channel 1 may be configured with greater width than depth to maximize solution contact area with membrane 3 while minimizing flow channel 1 dead volume. Minimum dead volume reduces sample carryover or band broadening when the charged droplet sprayer is used in ion sources interfacing liquid chromatography and mass spectrometry (LC/ES/MS) instruments. Membrane 3 separates conductive element 5 from sample solution 1A flow and serves as a seal surrounding flow channels 1 and 2 clamped between sprayer body components 6 and 8. Electrode 7 is electrically isolated from liquid flow channel 1 by dielectric body 8.

A first or sample solution 1A enters channel 1 through entrance tube 10, passes through flow channel 1 and tube 9 flow channel 11 exiting from exit tip 12 as a charged droplet spray. Sample solution 1A flow through channel 1 is delivered and controlled through upstream fluid delivery or separation system 13. Sample solution delivery system 13 may include but is not limited to a liquid chromatography separation system, syringe pump, solution reservoir or capillary electrophoresis system. A second gas or solution 2A enters channel 2 through tube 15, passes through channel 2 and exits through tube 16. Conversely, gas or solution 2A may enter channel 2 through tube 16 and exit through tube 15. Gas or solution 2A can be supplied from a gas or fluid delivery system 34 through connecting channel 14. As will be described in more detail below, gas or fluid delivery system 34 can be operated to change the second gas or solution composition during Electrospray ionization. Stepped or gradient second gas or liquid composition profiles can be run during Electrospray ionization under user or program control. Gas or fluid delivery system 34 can change second gas or solution 2A composition based on user input, time periods, software programmed profiles or in response to data dependent events.

When pneumatic nebulization is employed for charged droplet formation, nebulization gas 18 is supplied through entrance tube 19, passing through annulus 17 and exits as high velocity gas flow 20 surrounding exit tip 12. Nebulizer annulus tube 39 may be configured as an electrically conductive or as a dielectric material in the embodiment shown. Electrical potentials applied to ring electrode 21, endplate electrode 22 and capillary entrance electrode 23 form an electric field at exit tip 12 of flow channel 1 during charged droplet spraying. Electrical voltages are applied to electrodes 5, 7, 21, 22 and 23 through power supplies 27, 28, 29, 30 and 31 respectively through user or software control. In some operating modes, an electrical potential can be applied to an upstream conductive element in the first solution flow channel such as entrance tube 10, configured as a conductor, through power supply 32 when switch 33 is closed. Typically upstream conductive surfaces such as connecting tubing, fittings and/or LC pumps are connected to ground potential. When it is preferable to have no redox reactions occurring on conductive surfaces in the first solution flow channel 1, conductive elements in the upstream liquid delivery system flow channel can be electrically floated or disconnected from an electrical reference by opening switch 33. Alternatively, the first solution flow pathway 1, including tube 10 can be configured with dielectric material. In such an embodiment, the first solution flow channel is electrically isolated or floating. An electrically isolated fluid delivery system may comprise a dielectric or electrically floated syringe. When it is not practical to electrically float conductive surfaces in the upstream first solution flow channels, the voltage applied to electrode 5 can be set to minimize or prevent redox reactions from occurring on upstream first solution flow channel conductive surfaces during Electrospray ionization.

Charged droplets are produced using charged droplet sprayer 4 from solution 1A flowing through channel 1 and spraying from exit tip 12 by applying an electrical potential difference between electrode 5 and external electrodes 21, 22 and 23. Electrode 7 with voltage supply 28 may be included or removed from the charged droplet sprayer depending on the required operating mode. Electrode 21 may also be removed provided that appropriate electrical potentials are applied to the remaining counter electrodes 22 and 23 during charged droplet spraying. Tube 9 may comprise a dielectric material such as fused silica or PEEK (polyetheretherketone) or conductive material such as stainless or platinum. In the embodiment of the invention shown in FIG. 1, when tube 9 comprises a conductive material, it is electrically isolated in dielectric body 8 to prevent any redox reactions from occurring on the surface of channel 11 of tube 9 during charged droplet formation. Depending on the presence of connected conductive elements in flow channel 1, charged species transferred through membrane 3 in charged droplet sprayer 4 provide all or a portion of the charged droplet spray current during Electrospray ionization. Charged and/or neutral species passing through membrane 3 modify the composition of sample solution 1A during Electrospray ionization in the portion of flow channel 1 and 11 from membrane 3 to exit tip 12. During positive polarity charged droplet spraying, positive electrical potential is applied to electrode 5 relative to the electrical potentials applied to counter electrodes 21, 22 and 23. The electric field formed at exit tip 12 drives the movement of charged species in solution 1A along channel 11, in tube 9, along channel 1, through dielectric membrane 3 and across channel 2 to electrode 5.

In positive polarity Electrospray ionization operating mode with the appropriate gas or solution 2A flowing through channel 2 and the appropriate electrode material 5, such as graphite, protons (H+) are formed by an oxidation reaction occurring at the surface of cathode 5. Electrons flow from the surface of electrode 5 to power supply 27 as electric current. The protons formed move through semipermeable dielectric membrane 3 from channel 2 into channel 1, driven by the electric field, forming a net positively charged solution 1A in channel 1. Positively charged solution 1A passes through channel 1 and channel 11 and sprays from exit tip 12 forming positive polarity charged droplets. The charged species produced from evaporating positive polarity charged droplets that impinge on negative potential counter electrodes 22 and 23, neutralize by accepting electrons from power supplies 30 and 31, completing the electrical circuit for that portion of charge. A portion of the charged species formed from the evaporating charged droplets enter orifice 24 into vacuum and are mass analyzed by mass analyzer 35. The positive polarity charged species entering vacuum are neutralized by impinging on conductive surfaces or the mass spectrometer detector, completing the electrical circuit for that portion of charge produced. The positive polarity charged droplet spray removes positive charge from flow channel 1 and 2 effectively completing the electrical circuit with power supply 27. Typically, for an exit tip 12 to counter electrode 22 spacing of 1 to 2 centimeters, a 3,000 to 6,000 volt differential will be maintained between electrical potentials applied to electrode 5 and counter electrode 22 when electrode 21 is not present. Lower voltages are typically applied when smaller spacings are configured between counter electrode 22 and exit tip 12 to maintain a sufficiently high electric field at exit tip 12 to produce charged droplet spray 38 while avoiding gas phase breakdown, the formation of corona discharge or unstable Taylor cones. One or more Taylor cones may form at tip 12, without nebulization gas flow, producing charged liquid droplets through the Electrospray process. Alternatively, nebulization gas flow 20 can be applied to form charged liquid droplets through gas to liquid shear forces at exit tip 12 without the formation of a Taylor cone. Negative charged liquid droplets are formed by reversing the polarity of the relative potentials described above. In both positive and negative charged droplet production, electrode 5 may be maintained at or near ground potential with kilovolt potentials applied to counter electrodes 21, 22 and 23. Conversely, kilovolt potentials may be applied to electrode 5 with electrodes 21, 22 and 23 maintained closer to ground electrical potential.

When charged droplet sprayer 4 is configured in an atmospheric pressure ion source for mass spectrometry, the charged liquid droplets formed in spray 38 are directed toward counter electrodes 22 and 23 by the applied electric field against a heated counter current drying gas 25 flowing through opening 37 in endplate electrode 22. Heated counter current drying gas 25 aids in drying the charged liquid droplets formed in spray 38. As the charged liquid droplets evaporate, ions are formed and a portion of the ions are swept through orifice 24 into vacuum where they are mass to charge analyzed using mass to charge analyzer 35. Charged droplet sprayer 4 and alternative embodiments as described in the following sections may be used in other applications where charged liquid droplets or ions created from evaporating charge liquid droplets are required. Such applications may include spray painting or ion implantation on surfaces. The charged droplet sprayer may be configured with ion sources that employ gas phase charge exchange or charge impingement on surfaces. For example, the charged droplet sprayer 4 may be configured to direct charged droplets counter flow to a vaporized sample solution flow in an Atmospheric Pressure Chemical Ionization (APCI) source to provide a field of charged ions for gas phase charge exchange with vaporized gas phase sample molecules. In such an embodiment, charged droplet sprayer 4 eliminates the need for a corona discharge needle to create gas phase ions as configured in a conventional APCI source. In an alternative application, ions formed from the charged droplet sprayer can be directed to impinge on a sample target. Formation of sample ions from such sample target surfaces can be generated by collision of charge droplet sprayer generated ions with the surface, rapid reversal of the electric field at the surface after charging and with impingement of a laser pulse after charging of the surface as is described in pending U.S. Provisional Patent Application Ser. No. 60/573,666 incorporated herein by reference.

Figure 2:
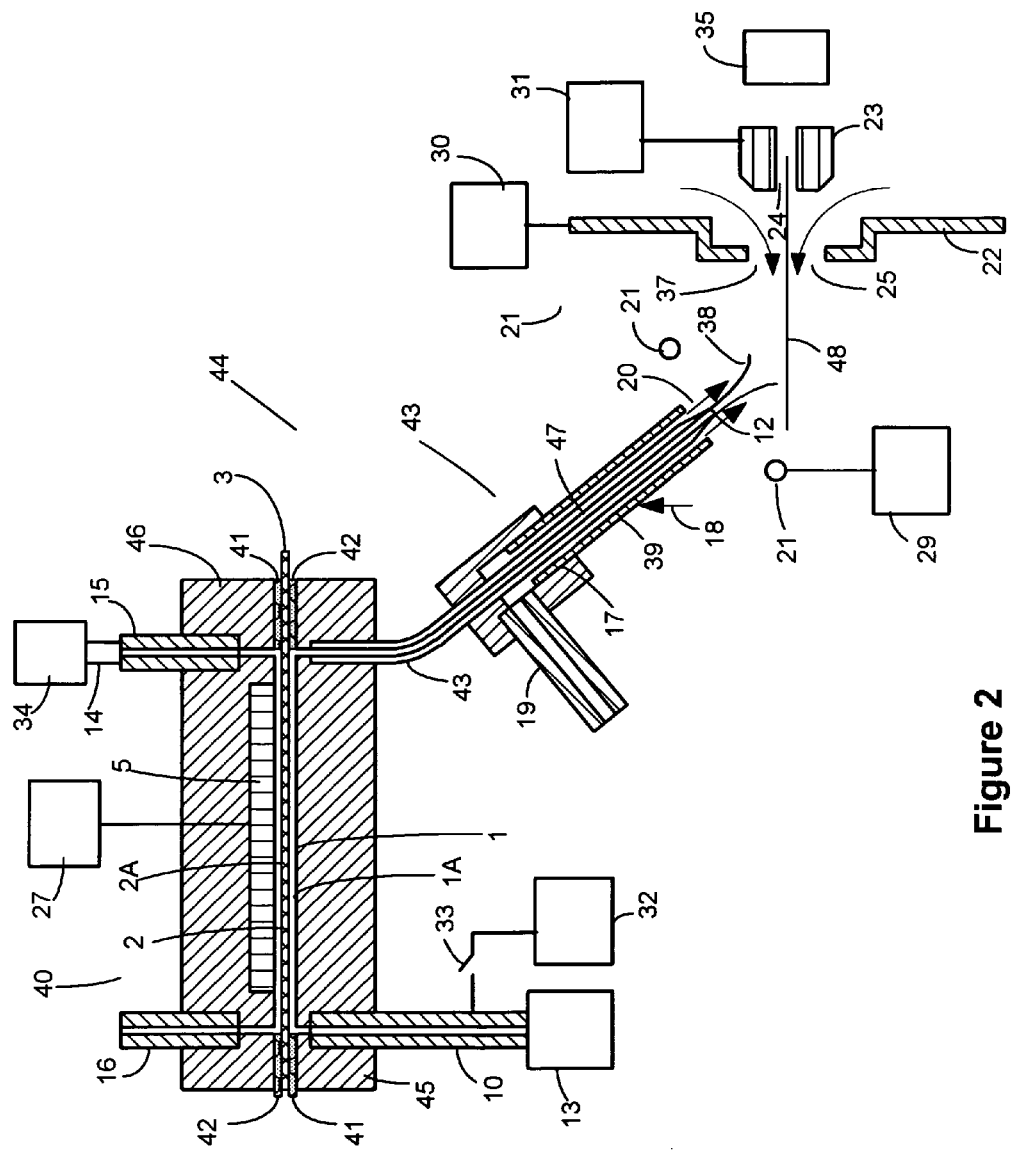
FIG. 2 is a cross section view of a two flow channel membrane assembly connected to a separate pneumatic nebulization charged droplet sprayer.
Figure 3:
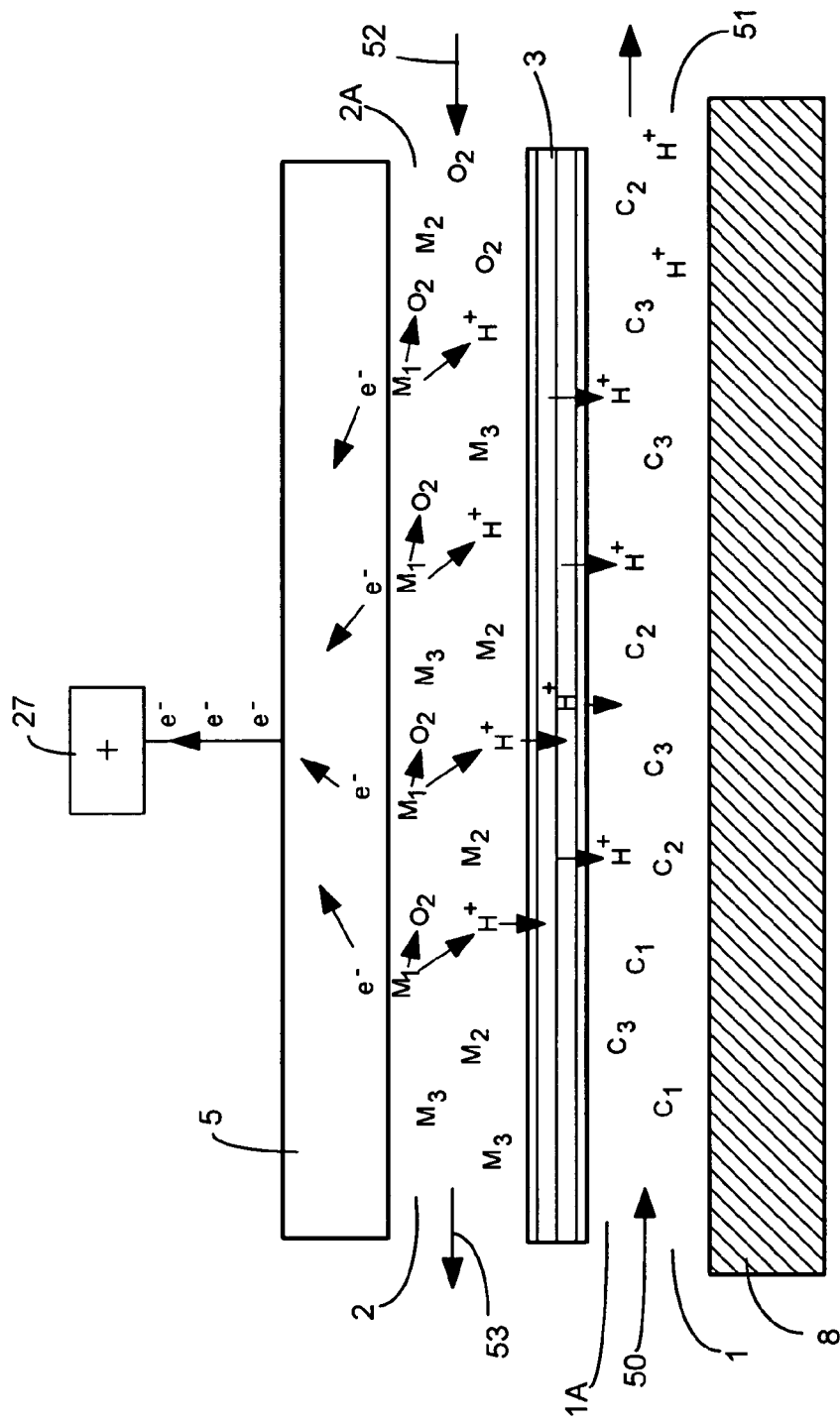
FIG. 3 is a diagram of an electrochemical reaction in second solution flow channel with proton exchange across the membrane of the charged droplet sprayer embodiment shown in FIGS. 1 and 2.

An alternative embodiment to the invention is diagrammed in FIG. 2. Pneumatic nebulizer sprayer assembly 43 is configured separate from two solution flow channel membrane assembly 40 in charged droplet sprayer assembly 44 shown in FIG. 2. All elements in FIG. 2 that are common to those elements shown in FIG. 1 retain the same numbers. Sample solution 1A flows through solution channel 1, through flow channel 47 in tube 43 and exits at tip 12 with pneumatic nebulization gas flow 20. Tube 43 comprises an electrically floating conductive material such as stainless steel or a dielectric material such as fused silica. Tube 43 can be connected to two flow channel membrane body component 45 using conventional means including, but not limited to, a ferrule and nut tubing connection. Sprayer assembly 43 is positioned at an angle relative to ion source centerline 48 to avoid spraying charged droplets into orifice 24 in higher liquid flow rate applications. Membrane assembly 40 body components 45 and 46 comprise flat surfaces that would form a flush contact against semipermeable membrane 3 without slotted gaskets 41 and 42. Dielectric slotted gaskets 41 and 42 are positioned between body components 45 and 46 respectively and membrane 3 in two flow channel membrane assembly 40. Gaskets 41 and 42, typically comprising a dielectric material, seal flow channels 1 and 2 when body elements 45 and 46 are clamped together. The cross sectional area of flow channels 1 and 2 are established by the gasket thickness and width of the opening or slot in gaskets 41 and 42 respectively. Body element 45 comprises a dielectric material and body element 46 comprises a dielectric or conductive material. When body element 46 is comprises a conductive material it is configured as electrically insulated from surrounding elements but in electrical contact with electrode 5. The separation of two flow channel membrane assembly 40 from pneumatic nebulization sprayer assembly 43 allows two flow channel membrane assembly 40 to be interfaced to commercially available pneumatic nebulization or unassisted Electrospray inlet probes in Electrospray mass spectrometer instruments.

The composition of sample solution 1A can be altered in flow channel 1 by the flow of charged and neutral species through membrane 3 during Electrospray ionization. Charged species are formed in flow channel 2 from electrochemical reactions occurring between gas or solution 2A present in flow channel 2 with the surface of electrode 5 in the presence of an electric field. Charged species formed from electron transfer between solution or gas 2A and electrode 5 are transferred through membrane 3 driven by the same electric field. FIG. 3 is a cross section diagram of flow channels 1 and 2, membrane 3, electrode 5 and dielectric body 8 or 45 in charge droplet sprayers 4 and 44 as shown in FIGS. 1 and 2. FIG. 3 is a diagram of one example of the formation of positive charged species and exchange of charged species from solution 2A into solution 1A across membrane 3 in positive polarity Electrospray ionization. Sample solution 1A enters flow channel 1 at end 50 comprising molecular species $C_1$, $C_2$ and $C_3$ that ultimately form protonated ions from sprayed charged droplets provided each species has sufficient proton affinity. Second solution 2A flows through flow channel 2 entering at end 52 and exiting at end 53 comprising molecular species $M_1$, $M_2$ and $M_3$. Charged species move across channel 2 from electrode 5 through membrane 3 driven by application of an electric field at Electrospray tip 12 as described above. Charged species passing through flow channel 1 through exit end 51 during Electrospray ionization form a portion of the electric circuit terminating in the example shown at the positive polarity end with power supply 27. In the example shown in FIG. 2, the $M_1$ species is water ($H_2O$) and $M_2$ and $M_3$ species comprise an appropriate electrolyte, such as hydrochloric acid, acetic acid or a salt to aid in the electrolysis of water at the surface of electrode 5. The surface of electrode 5 may comprise silver, silver chloride, carbon, gold, platinum black, platinum, stainless steel or other appropriate material that will maximize electrolysis efficiency but minimize electrode erosion.

When operating in positive polarity charged droplet spray mode, a positive electrical potential is maintained on electrode 5 using power supply 27 relative to the potentials applied to counter electrodes 22 and 23. Electrolysis of water molecules $M_1$ occurs at electrode 5 forming H+, oxygen ($O_2$) and other species as described by Van Berket et. al.[4]. $H^+$ is driven by the electric field across channel 2 toward membrane 3. Membrane 3 comprises an appropriate material to selectively facilitate proton transfer through the membrane but provides an otherwise inert impermeable dielectric surface to solution 1A in channel 1 and solution 2A in channel 2. In one preferred embodiment of the invention, membrane 3 material comprises sulfonated fluoroethylene material, (perfluorsulphonic acid polytetrafluoroethylene (PTFE) copolymer) one formulation of which is Nafion (® Dupont). Nafion is a fluorethylene polymer with sulfonated side chains terminating with an ironically bonded sulphonic acid ($HSO_3$) that forms an $SO_3^{2}$ ion at the side chain termination. The hydrophyllic property of the sulphonic acid groups causes local hydration of an otherwise hydrophobic material. Other membrane materials, including but not limited to, cellulose esters and polysulfone dialysis tubing with different molecular weight cutoffs or cation or anion semipermeable membranes available from Dionex corporation may be configured as membrane 3. Specific membranes can be used that maximize performance for a given applications. The same or different material membranes can be layered to enhance specific species permeability while selectively blocking unwanted species. Individual membrane materials such as Nafion will pass selected charged species driven by an electric field and selected neutral species driven by concentration gradients between solutions 1A and 2A on opposite sides of membrane 3. Such ion and neutral selectivity can be exploited to enhance performance in Electrospray MS analysis. The performance of a Nafion membrane during Electrospray ionization is described below as one example of a type of membrane material that can be used in the embodiments of the invention shown in FIGS. 1 and 2.

Driven by the electric field across membrane 3, $H^+$ ions are able to pass through the Nafion membrane moving along the hydrated sulfonated side chain groups due to the relatively weak attraction of the $H^+$ to the hydrated $SO_3^{2}$ ion. Nafion is commonly employed in fuel cell technology to selectively transport $H^+$ ions from one flow chamber to another. The use of Nafion provides a chemically inert surface to solutions 1A and 2A flowing through channels 1 and 2 respectively, while allowing the transfer of protons across the membrane with minimum transport of unwanted chemical species into solution 1A. Protons move through membrane 3 driven by the electric field adding protons into solution 1A flowing through channel 1. This $H^+$ charge transfer forms a net increase in a positive polarity charge in solution 1A flowing through channel 1, without the addition of anion species, supplying positive polarity charge during the formation of positively charged droplets spraying from exit tip 12. Electrical potential can be applied to electrode 7 to promote or inhibit charge exchange across membrane 3, however, the potential applied to electrode 7 exerts less influence on the charge transfer process than the relative electrical potentials applied between electrode 5 and counter electrodes 21, 22 and 23. 100% aqueous solution, without acid, can be used as solution 2A flowing through channel 2 minimizing conductance and reducing the total charged droplet current produced from solution 1A. Proton current transferred across membrane 3 can be increased for the same relative electrical potentials applied to electrode 5 and counter electrodes 21, 22 and 23 by increasing the concentration of acid in solution 2A.

The total current produced from solution 1A sprayed from exit tip 1 can be increased by increasing the concentration of electrolyte in solution 2A flowing through channel 2. The increase in positive polarity spray current produced by increasing the concentration of acid in solution 2A is similar to that achieved by increasing the concentration of acid in solution 1A in conventional Electrospray ionization. In the embodiment of the invention shown in FIGS. 1 and 2, charged droplet sprayers 4 and 44 are configured having no connected conductive elements in the first solution 1A flow channel 1. Electrode-solution electrochemical reactions occur on surfaces external to the first solution 1A flow path during charged droplet spraying. The total charged droplet spray current produced from charge droplet sprayers 4 or 44 can be varied by changing the pH or concentration of acid of solution 2A in channel 2. The concentration of acid can be changed as a step function or gradient during Electrsprah operation using fluid delivery system 34. For example, a gradient LC or dual syringe pump can be used for fluid delivery into channel 2. If the solution in the first syringe is water and the solution in the second syringe contains water with hydrochloric acid, then the ratios of the two solutions can be controlled by the LC gradient or dual syringe pump prior to delivery to channel 2 of charged droplet sprayer 4 or 44. Alternatively, fluid delivery system 34 can be one half of an electrolysis cell comprising a Nafion or other appropriate semipermeable membrane. The voltage applied across electrodes in the electrolysis cell will determine the concentration of protons delivered to solution 2A. Software controlled fluid delivery system 34 can be can be programmed to generate specific charged droplet spray currents from Electrospray tip 12 by controlling the rate of charge species transfer into or out of solution 1A through membrane 3. Charged droplet spray currents can be controlled in this manner without changing exit tip 12 to counter electrode 22 and 23 geometries or changing the relative voltages applied between electrode 5 and counter electrodes 21, 22 and 23. Slow or rapid pH or conductivity scans in solution 1A can be conducted by stepping or ramping the pH in solution 2A during Electrospray ionization.

Figure 4A:
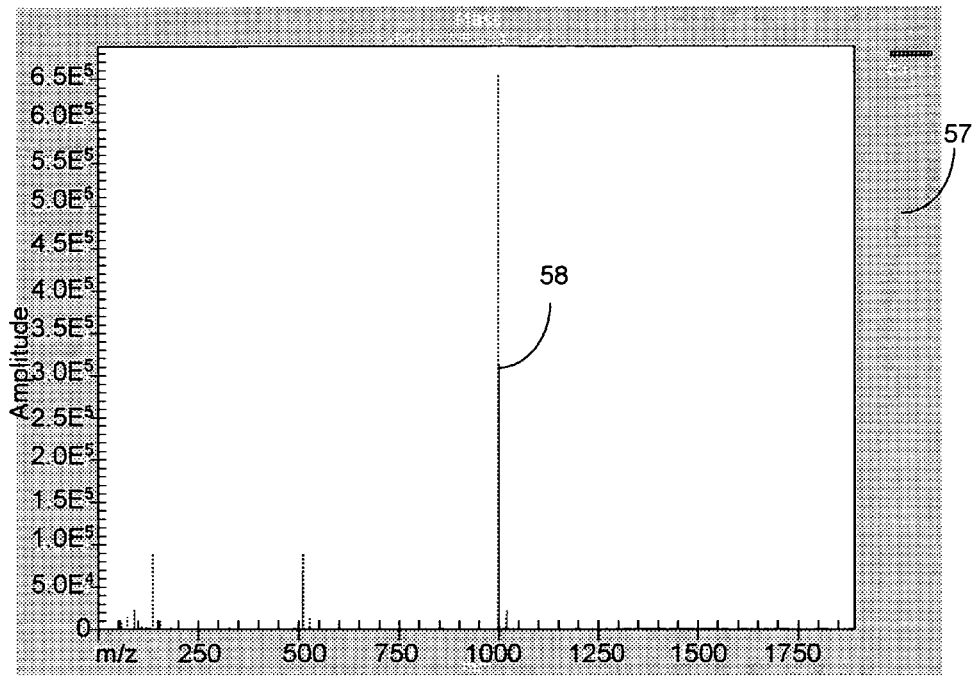
FIG. 4A is a mass spectrum of hexatyrosine sprayed from a 100% aqueous solution using the charged droplet sprayer embodiment shown in FIG. 1.
Figure 4B:
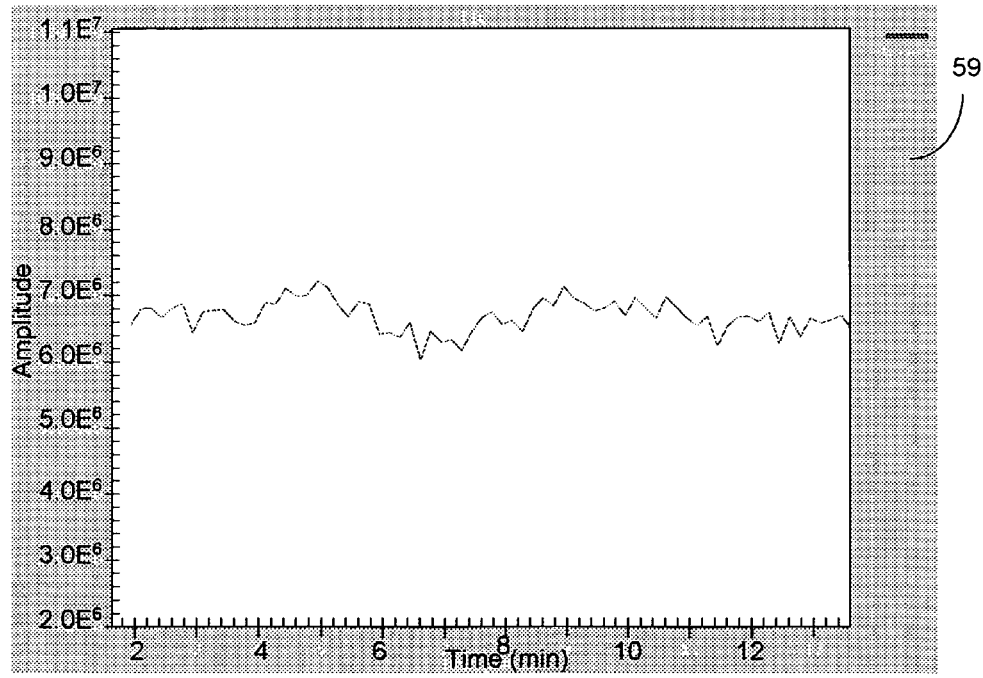
FIG. 4B is an extracted ion chromatogram of hexatyrosine in a 100% aqueous solution sprayed from the charged droplet sprayer embodiment shown in FIG. 2.

FIG. 4A is a mass spectrum of hexatyrosine Electrosprayed from a 100% aqueous solution 1A using charged droplet sprayer 44 with a 100% aqueous solution 2A flowing through channel 2 at a flowrate of 3 ul/min. Tube 43 in charged droplet sprayer 44 comprised a fused silica tube with no pneumatic nebulization used while acquiring spectra 57. The amplitude of hexatyrosine peak 58 was stable during acquisition as shown in extracted ion chromatogram 59 plotted in FIG. 4B. Solution 1A was not in contact with conductive elements during charged droplet spraying so all electrochemical reactions occurred on conductive surfaces external to the first solution flow path 1A. Acquisition of mass spectrum 57 with MS signal stability comparable to that shown in FIG. 4 when Electrospraying a 100% aqueous solution without pneumatic nebulization assist is more difficult to achieve using conventional Electrospray probes with metal tips. The charged droplet sprayer allows the stable Electrospraying of solutions that would be difficult to achieve with standard conductive tip Electrospray probes configured with redox reactions occurring on conductive surfaces in the first sample solution flow path.

Figure 5A:
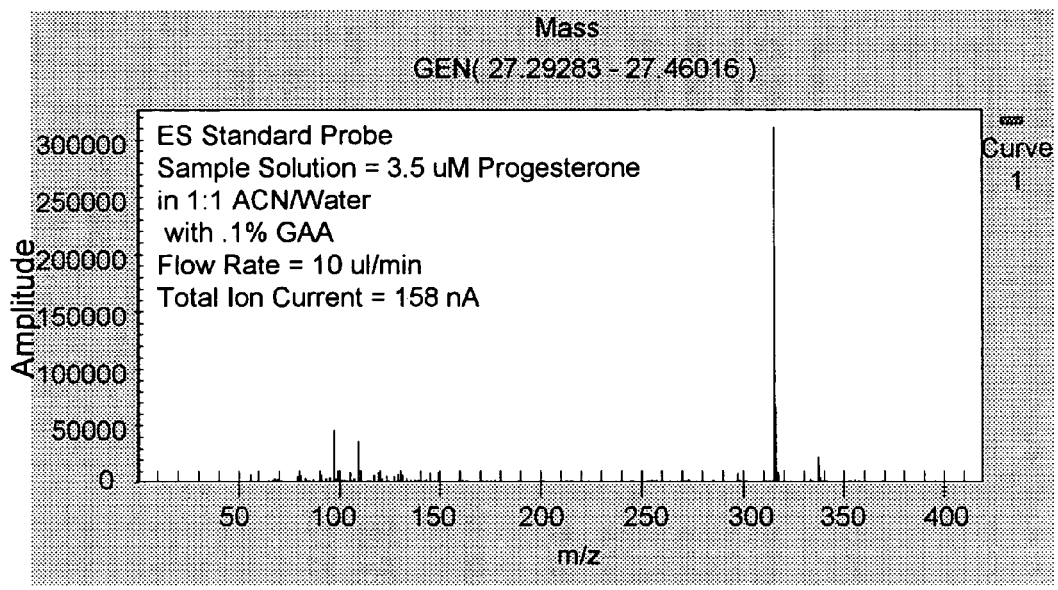
FIG. 5A is a mass spectrum of a 3.5 µM solution of Progesterone in a 1:1 acetontrile:water, 0.1% glacial acetic acid sprayed using a conventional Electrospray probe.
Figure 5B:
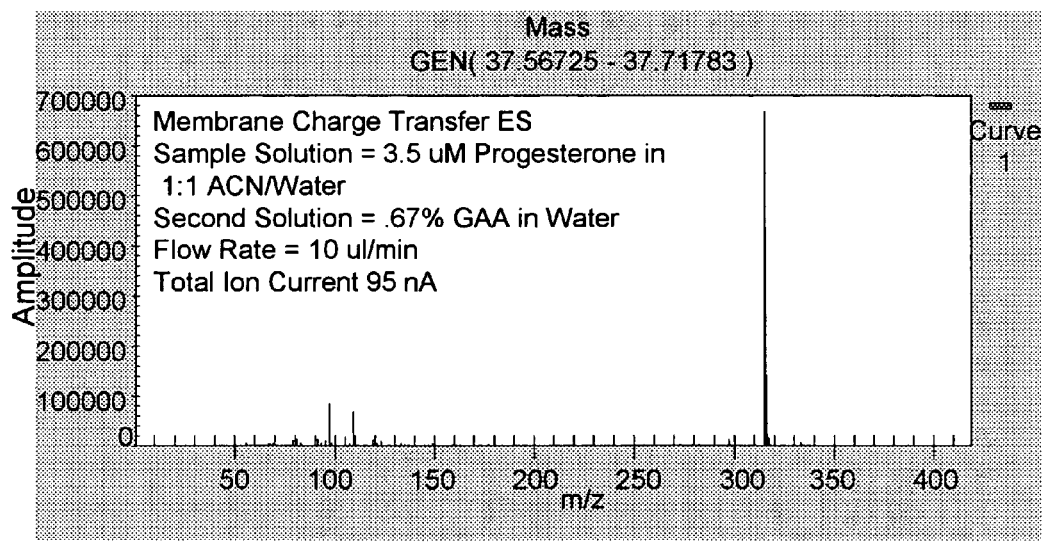
FIG. 5B is a mass spectrum of a 3.5 µM sample solution of Progesterone in a 1:1 acetontrile:water with a 0.67% glacial acid in water second solution sprayed from the charged droplet sprayer embodiment shown in FIG. 2.

FIG. 5 shows a set of ES-MS spectra of progesterone run with a standard conductive tip Electrospray probe and charged droplet sprayer 44 as diagrammed in FIG. 2, both using pneumatic nebulization assist. FIG. 5A shows the positive polarity mass to charge spectrum of the protonated molecular ion of a 3.5 μM (3.5 pm/μl) solution of progesterone, $(M+H)^+ = 315.2$ m/z, in a 1:1 acetonitrile:water with 0.1% acetic acid Electrosprayed at 10 μl/min. The total Electrospray current was 158 nanoamps exceeding the minimum of 56 nanoamps total Electrospray current required to fully protonate 3.5 μM of singly charged sample ions Electrospraying at a liquid flow rate of 10 μl/min. FIG. 5B shows a mass to charge spectrum of the same 3.5 μM solution of progesterone in a 1:1 acetonitrile:water solution with no acetic acid added while Electrospraying from the charged droplet sprayer 44 at a flow rate of 10 μl/min. Solution 2A flowing through channel 2 was water with 0.2% acetic acid producing a total Electrospray current of 95 nA. The progestone $(M+H)^+$ peak amplitude increased over a factor of two from the maximum signal achieved using the standard Electrospray probe. Running a pH gradient with hydrochloric acid (HCL) added to solution 2A with 1:1 acetonitrile:water solution instead of acetic acid produced a comparable $(M+H)^+$ signal at a 1% HCL acid concentration in solution 2A with a total Electrospray current of 275 nA. All MS spectra shown were acquired using and Analytica of Branford, Inc. atmospheric pressure ion source orthogonal pulsing Time-Of-Flight mass spectrometer.

Figure 6A:
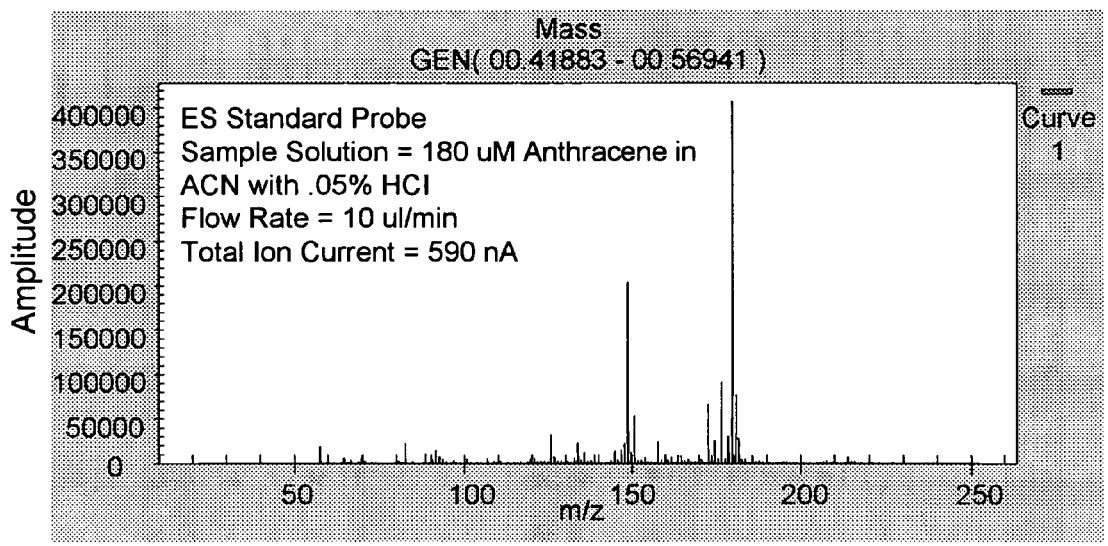
FIG. 6A is a mass spectrum of a 180 µM solution of Anthracene in Acetontrile with 0.5% HCL sprayed using a conventional Electrospray probe.
Figure 6B:
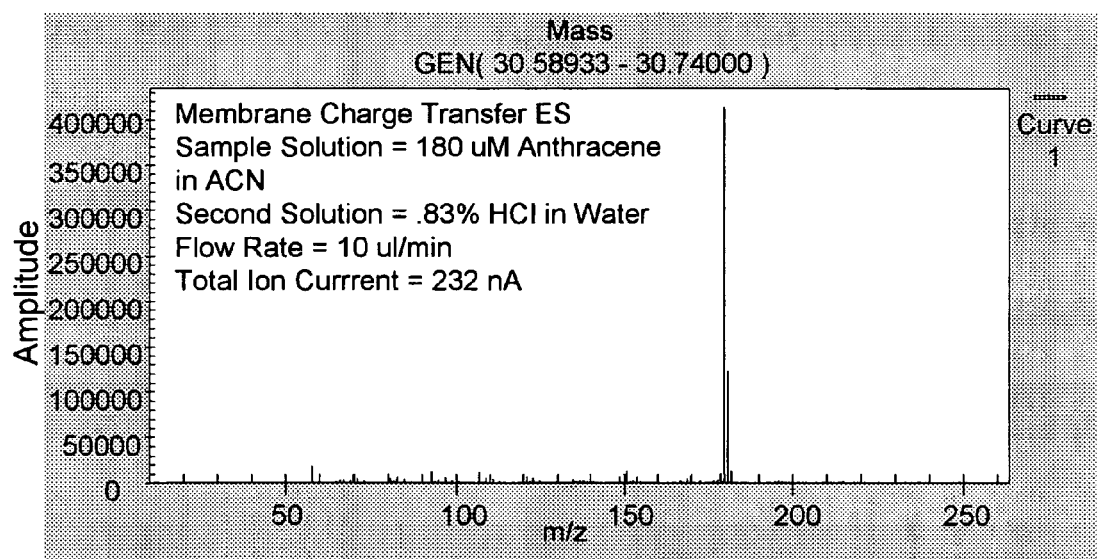
FIG. 6B is a mass spectrum of a 180 µM sample solution of Progesterone in acetontrile with a 0.83% HCL in water second solution sprayed from the charged droplet sprayer embodiment shown in FIG. 2.
Figure 7:
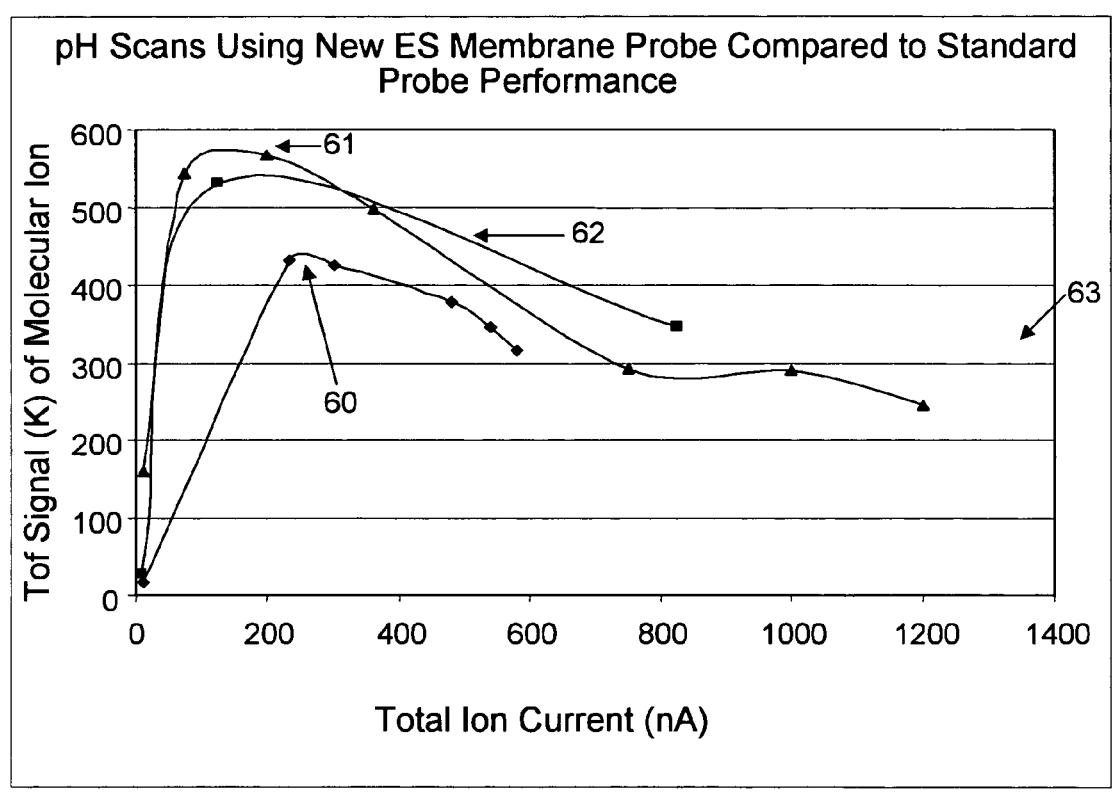
FIG. 7 is an extracted ion chromatogram for Hexatyrosine and Anthracene running pH scans in the second solution while spraying from the charged droplet sprayer embodiment shown in FIG. 2 compared to conventional Electrospraying with increasing acid concentration in the sample solution.

Improved mass spectrum quality can be achieved using charge droplet sprayers configured according to the invention. Eliminating the need to add acids, bases, salts or buffer species to the sample solution to increase solution conductivity or to buffer or modify pH avoids the addition of contamination species included in such added species solutions. FIG. 6A is a positive polarity mass spectrum of the molecular ion of non polar Anthracene acquired by Electrospraying a solution 1A of 180 μM Anthracene in acetonitrile with 0.05% HCL acid using a standard ES probe. The total ES ion current was 590 nA and several contaminate peaks, possibly added with the HCL acid, are present in the mass spectrum. FIG. 6B is a mass spectrum of a 180 μM solution of Anthracene in acetonitrile acquired by Electrospraying at 10 μl/min using the charged droplet sprayer 44 as diagrammed in FIG. 2 with a 1% HCL acid in water solution 2A flowing through channel 2. The total ES current during MS acquisition was 232 nA. The amplitude of the molecular ion peak is consistent in both spectrum, however, the mass spectrum acquired using the charged droplet sprayer 44 shows fewer contamination peaks. PH scans in solution 1A can be conducted during Electrospray ionization using charged droplet sprayers 4 or 44, configured according to the invention. Curve 60 of graph 63 in FIG. 7 shows a pH scan conducted for Anthracene using the charged droplet sprayer 44 where the concentration of HCL in water was ramped in second solution 2A during Electrospraying of a 180 μM solution 1A of anthracene in acetonitrile. As the HCL concentration increased in second solution 2A, the total ES current increased. The maximum anthracene signal was achieved at approximately 250 nA total ES current. Signal response curves 61 and 62 for a 1 μM solution of hexatyrosine in 1:1 methanol:water versus total ES current are also shown in graph 63 of FIG. 7. Curve 61 was generated using a pH gradient with HCL acid in water run in second solution 2A while Electrospraying the above hexatyrosine sample solution 1A at 10 μl/min. For direct comparison, curve 62 is a signal response curve of the same hexatyrosine sample solution 1A sprayed from a conventional Electrospray probe with increasing concentrations of HCL added directly to sample solution 1A.

Figure 8A:
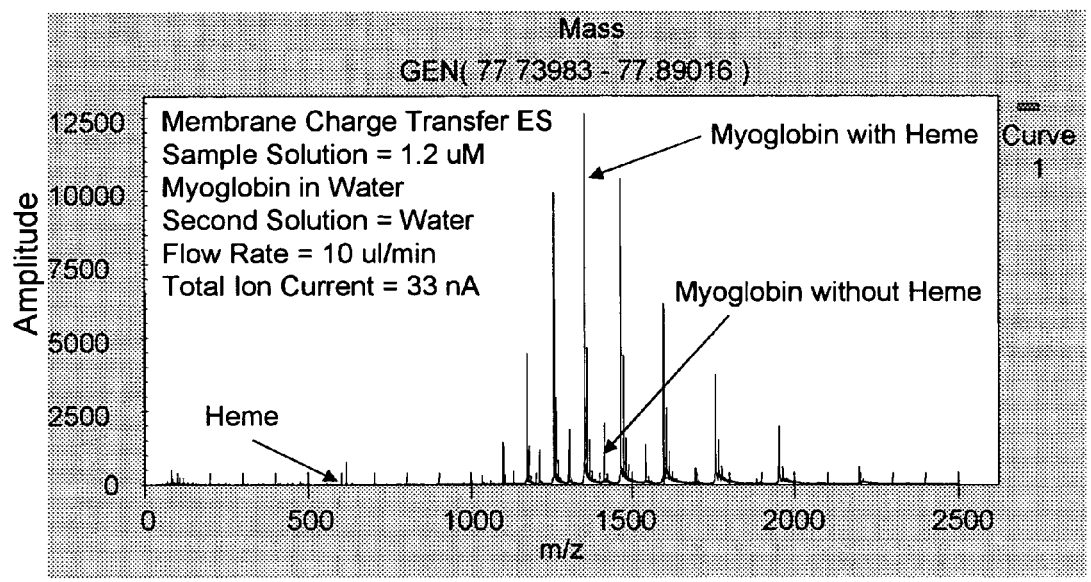
FIG. 8A is a mass spectrum of a 1.2 µM solution of Myoglobin in water with a 100% aqueous second solution sprayed from the charged droplet sprayer embodiment shown in FIG. 2.
Figure 8B:
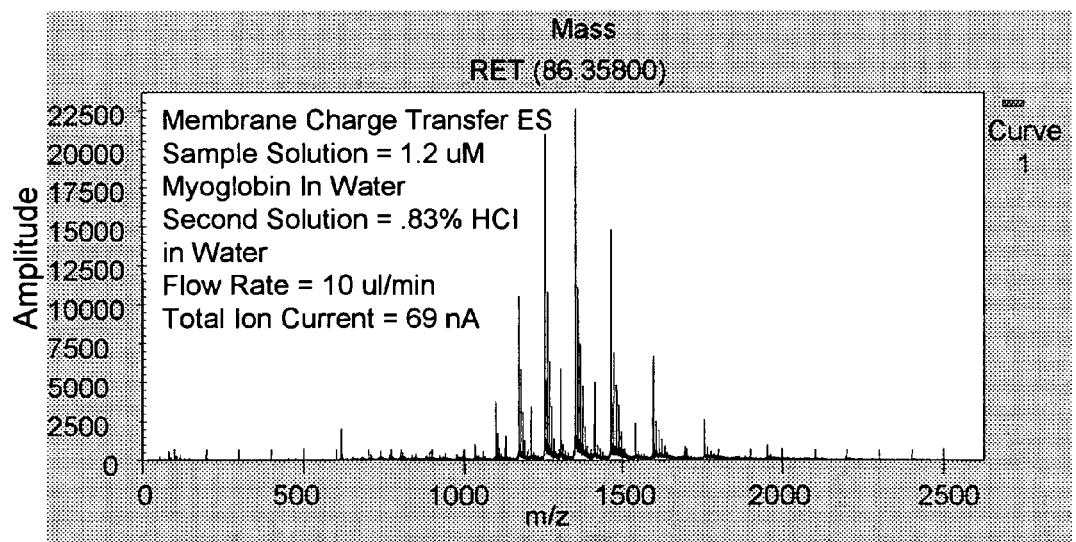
FIG. 8B is a mass spectrum of a 1.2 µM solution of Myoglobin in water with a 0.83% HCL in water second solution sprayed from the charged droplet sprayer embodiment shown in FIG. 2.
Figure 8C:
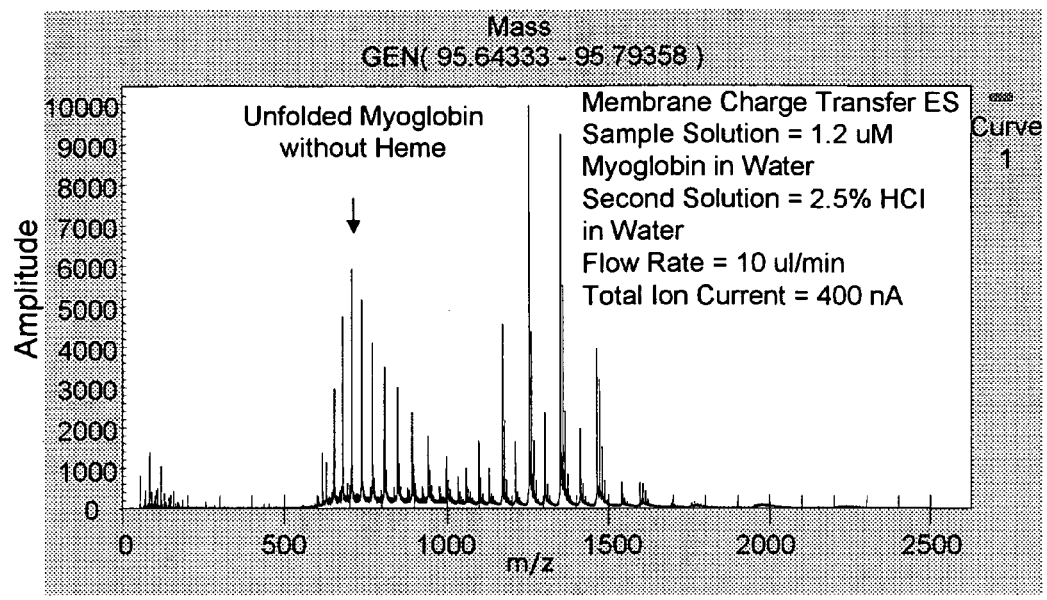
FIG. 8C is a mass spectrum of a 1.2 µM solution of Myoglobin in water with a 2.5% HCL in water second solution sprayed from the charged droplet sprayer embodiment shown in FIG. 2.
Figure 8D:
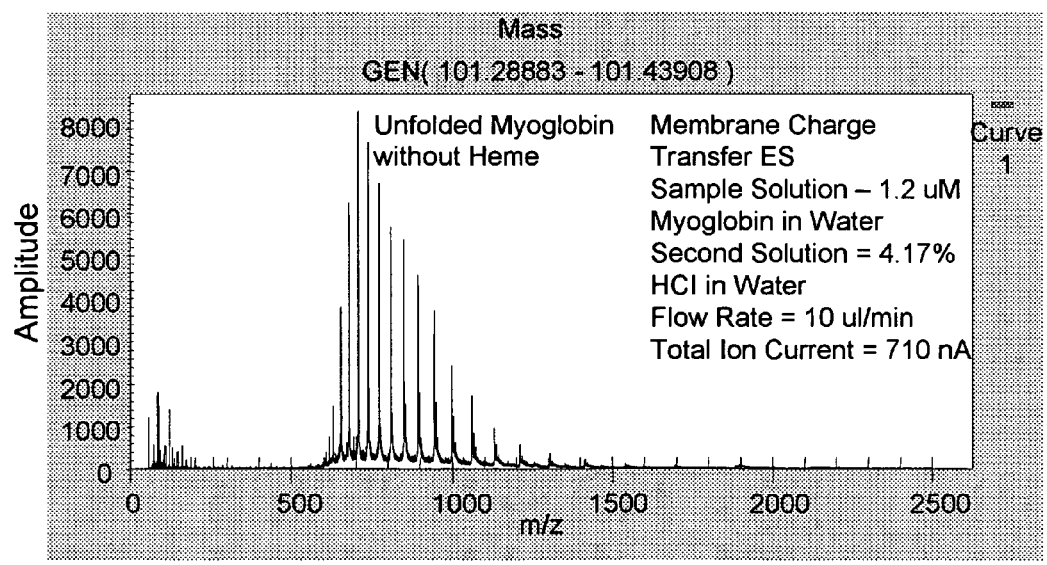
FIG. 8D is a mass spectrum of a 1.2 µM solution of Myoglobin in water solution with a 4.17% HCL in water second solution sprayed from the charged droplet sprayer embodiment shown in FIG. 2.

PH scans can be conducted during Electrospray ionization to study protein and noncovalently bound compound conformations using the new charged droplet sprayers configured according to the invention. FIG. 8 shows the changes in ES-MS spectra acquired during Electrospraying of a 1.2 μM aqueous solution 1A of horseheart Myoglobin while running a rapid pH gradient in solution 2A. The concentration of HCL acid in aqueous solution 2A was ramped using charged droplet sprayer 44 during pneumatic nebulization assisted Electrospray ionization. FIG. 8A shows the ES-MS spectra with a 100% aqueous solution 2A producing a total ES current of 33 nA. The signal amplitude is reduced due to a limit in total available charge. A high percentage of the myoglobin in the aqueous sample solution remains in a folded configuration retaining the heme group. The observed adduct peaks are due to contaminant species present in the Myoglobin sample purchased from Sigma. As the HCL acid concentration in solution 2A is ramped, increasing the total ES ion current and lowering the pH in solution 1A, the myoglobin molecule begins to unfold in solution and loses the heme group as shown progressively in FIGS. 8B, 8C and 8D. In the series of mass spectra acquired in FIG. 7, sample solution 1A flow was constant with charged species added only through membrane 3 of the charged droplet sprayer 44. Charged droplet sprayer 44 can be operated by rapidly scanning total ES ion current and/or pH in solution 1A with little or no addition of contamination species to sample solution 1A. Adjustment of conductivity and the composition of charged species in solution 2A allows rapid optimization of ES/MS performance to achieve maximum analyte signal for the same sample solution. This capability is particularly useful in providing optimal ES/MS performance in high throughput and target compound analysis. Changes in confirmations of proteins or non covalently bound compounds in solution that are observable through shifting multiply charged peak patterns and losses of non covalently bound groups can be rapidly scanned to provide additional information when studying protein or non covalently bound complex structures.

Figure 9:
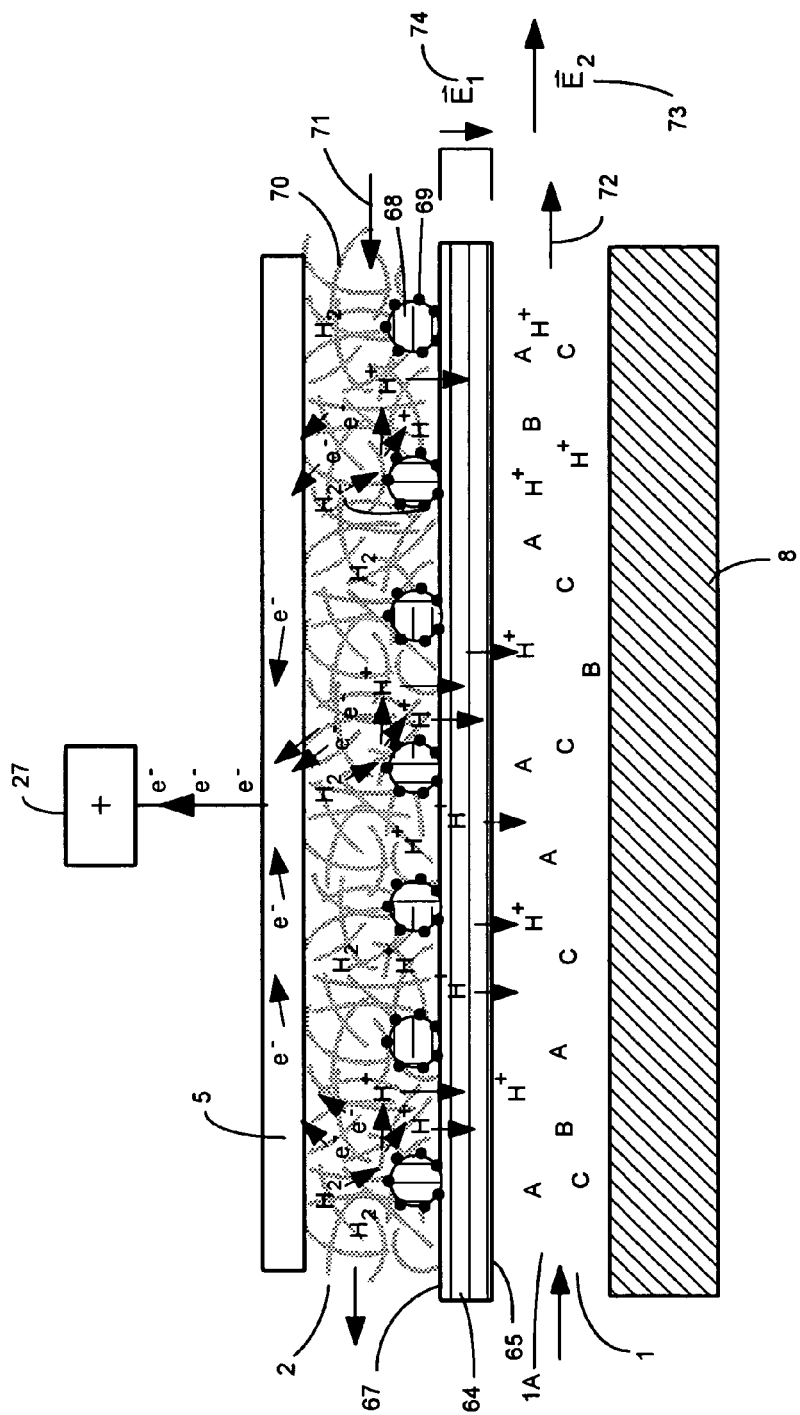
FIG. 9 is a diagram of a hydrogen gas oxidation reaction in the second flow channel with proton transport across the membrane in the charged droplet sprayer embodiment shown in FIGS. 1 and 2.

In alternative embodiments to the invention, different types of materials can be used for semipermeable membrane 3 in charged droplet sprayers 4 and 44 to maximize analytical performance for specific applications using positive or negative polarity Electrospray ionization. FIG. 9 shows a cross section view of the flow channels 1and 2 separated by an alternative membrane 64 configured to facilitate ionization of hydrogen gas flowing through channel 2. Hydrogen gas is ionized on the surfaces of platinum particles 69 embedded in carbon electrode supports 68 located in flow channel 2. Semipermeable membrane 64 contacts solution 1A in flow channel 1 along membrane surface 65. Membrane 64 can be hydrated by water in solution 1A or by water vapor added to the hydrogen gas flowing through flow channel 2. Along membrane surface 67 in contact with flow channel 2, carbon electrodes 68 imbedded with platinum catalyst particles 69 are bonded to surface 67 of semipermeable dielectric membrane 64. Porous carbon fiber mat 70 electrically connects carbon electrodes 68 to electrode 5. This carbon supported platinum catalyst material is well known in fuel cell technology (Fuel Cell Systems Explained, J. Larminie and A. Dicks, John Wiley and Sons, 2003, Chapter 4)[13] and is used as a conductive surface to ionize hydrogen in such devices. Hydrogen gas is ionized at the surface of the platinum particles forming protons with electrons removed through electrode 5 to power supply 27. The protons or H+ ions pass through semipermeable membrane 64 into sample solution 1A driven by electric field 74 sustained during Electrospray ionization. Ion current passes along flow channel 1 driven by sample solution flow 72 and electric field 73. Ion current exits flow channel 1 as charged droplets forming at exit end 12. The total Electrospray current can be controlled by adjusting the flow rate or concentration of hydrogen gas flow 71 passing through flow channel 2. Positive polarity charged droplet spray is produced from solution 1A using charged droplet sprayer membrane 64 with proton transfer through membrane 64 into solution 1A as shown in FIG. 9. Alternatively, negative polarity charged droplet production can be produced by configuring semipermeable membrane membrane 64 with the appropriate material to produce negative polarity ions from oxygen or other appropriate gas flowing through flow channel 2. Negative polarity ions move through semipermeable membrane 64 driven by the Electrospray electric field. In an alternative embodiment of charged droplet sprayers 4 or 44, electrode 5 can be configured with a platinum surface to catalyze the ionization of hydrogen gas to form protons that move across channel 2 through membrane 3 into solution 1A driven by the Electrospray electric field.

Negative polarity charge droplet sprays are generated by transferring protons or positive ions across membrane 3 from solution 1A to gas or solution 2A or by passing negative ions produced in gas or solution 2A into solution 1A through membrane 3 driven by the negative polarity Electrospray electric field. Different materials can be used for semipermeable membrane 3 to selectively transport specific anion species or electrons from channel 2 to channel 1 in negative polarity charged droplet production. When orifice 24 is configured as a dielectric capillary orifice into vacuum as described in U.S. Pat. No. 4,542,293 incorporated herein by reference, electrode 5 can be operated at ground potential in both positive and negative ion polarity. In positive polarity Electrospray ionization, −4,000 V and −5,000 V are applied typically applied to electrodes 22 and 23. Voltage polarity is reversed for negative polarity Electrospray ionization. With close to ground potential applied to electrode 5 during positive or negative Electrospray ionization, minimum redox reactions occur in the sample solution on grounded upstream conductive surfaces in flow channel 1 during Electrospray ionization. Preventing redox reactions occurring on conductive surfaces upstream of flow channel 1 minimizes changes in sample composition prior to Electrospray ionization. Minimizing changes to sample composition caused by redox reactions in the sample solution flow path increases Electrospray MS analysis quantitative and qualitative accuracy, consistency and reliability. The electrical current produced from redox reactions upstream of flow channel 1 can be measured by closing switch 33 connecting conductive tube 10 with power supply and current meter 32. The voltage applied to electrode 5 through power supply 27 can be adjusted to zero the electrical current produced at tube 10 by neutralizing the electric field upstream of flow channel 1 that may cause redox reactions to occur on conductive surfaces. For example, a small positive potential above zero volts applied to electrode 5 during positive polarity Electrospray ionization, minimizes redox reactions from occurring on upstream grounded conductive surfaces. The small positive electrical potential offset applied to electrode 5 counters the slightly negative electric field relative to ground extending through flow channel 1 with the above listed kilovolt potentials applied to electrodes 22 and 24. This results in a neutral or ground potential extending upstream from flow channel 1 preventing redox reactions on grounded upstream conductive surfaces.

Electrospray ion sources that are not configured with a dielectric capillary orifice into vacuum are typically configured with a conductive orifice or heated conductive capillary orifice between atmospheric pressure and the first vacuum pumping stage. A conductive orifice into vacuum is typically operated closer to ground potential during Electrospray ionization. Electrospray ion source configured with conductive orifices into vacuum can be operated with positive and negative kilovolt potentials applied to electrode 5 during positive and negative polarity Electrospray ionization respectively. Applying kilovolt electrical potentials to electrode 5 may result in generation of current on grounded conductive surfaces upstream of flow channel 1 due to electrochemical reactions in solution 1A. These upstream electrochemical reactions in solution 1A can be avoided by eliminating or electrically floating conductive surfaces configured upstream of flow channel 1. It is known in Electrospray operation where redox reactions occur on first solution flow channel conductive surfaces, that anion or cation species can be deposited on these conductive surfaces. When positive polarity Electrospray is switched to negative polarity Electrospray, anion species deposited on conductive surfaces can reenter sample solution 1A as contamination species. Redox reactions occur on surfaces external to the first solution 1A flow path in the charged droplet sprayer embodiments 4 and 44 shown in FIGS. 1 and 2, avoiding deposition of contamination species on conductive surfaces in the first solution 1A flow path. Operation of charged droplet sprayers 4 or 44 also avoids the buildup of deposited species that can ultimately block flow channels. When stainless steel Electrospray needles are configured as spray tips in conventional Electrospray operation, metal ions from the stainless steel may be produced due to the redox reactions occurring on the inner wall of the Electrospray needle. These metal ions present in the Electrospray solution produce unwanted contaminant ion peaks in the acquired mass spectrum. Deplating of metal Electrospray needles or stainless steel conductive surfaces in the sample solution flow path during Electrospray operation can be prevented using the charged droplet sprayer embodiments 4 and 44 shown in FIGS. 1 and 2.

A single stable Electrospray Taylor cone can deliver a limited amount of charged droplet spray current. Above this limit, the Taylor cone and the charged droplet production from the Taylor cone will become unstable. Total Electrospray current can be increased by increasing the conductivity in a first or sample solution of 1:1 methanol:water by the addition of acid (or salts) or through the addition of electrolytes in solution 2A in charged droplet sprayers 4 and 44. A single Electrospray Taylor cone can become unstable if total charged droplet spray current exceeds a value that is a function of solution composition, liquid flow rate, needle and spray tip geometry, solution flow path geometry, electrode geometry and applied voltage. For example, a Taylor cone formed when Electrospraying a methanol: water: acid solution at 5 µl/min may become unstable between 200 and 300 nanoamps total Electrospray current. FIG. 10A is a diagram of a stable Electrospray Taylor cone 83 formed from solution 82 flowing through tube 84 producing evaporating charged droplet spray plume 81 moving toward counter electrode 80. The initial charged droplets are produced in Electrospray with approximately one half the Rayleigh limit of charge. With a constant flow rate of solution 82 through tube 84, an increase in total Electrospray current requires that an increasing number of droplets are produced with a reduced droplet size distribution. An increased number of smaller size droplets provides additional total surface area, increasing the charge carrying capacity of the spray. As described above, the total charged droplet current produced from charged droplet sprayer 4 or 44 can be increased by increasing the conductivity or electrolyte concentration in solution 2A flowing through channel 2. As the charged droplet spray current increases, charged droplet plume 81 fans out due to increased charged droplet space charge repulsion. When the charged droplet spray current exceeds the stability limit of a single Electrospray Taylor cone, multiple spray plumes 85 and 86 form from tube 84 exit tip 87 as diagrammed in FIG. 10B. Stable single or multiple charged droplet spray plumes are produced using charged droplet sprayer 4 or 44 with first solution 1A comprising 1:1 methanol:water flowing at 5 µl/min with the addition of protons to solution 1A through membrane 3. Comparably stable sprays are difficult to achieve with conventional Electrospray apparatus using conductive Electrospray needle tips. Currents exceeding 300 nanoamps can be achieved with stable multiple Electrospray plume charged droplet spraying of 1:1 methanol:water solutions 1A from single exit tip 12 using the charged droplet sprayer embodiments 4 and 44 shown in FIGS. 1 and 2 without pneumatic nebulization. To achieve increased total charged droplet spray current capacity from charged droplet sprayers 4 and 44, multiple spray tips can be configured from flow channel 1 as diagrammed in FIG. 11.

Figure 11:
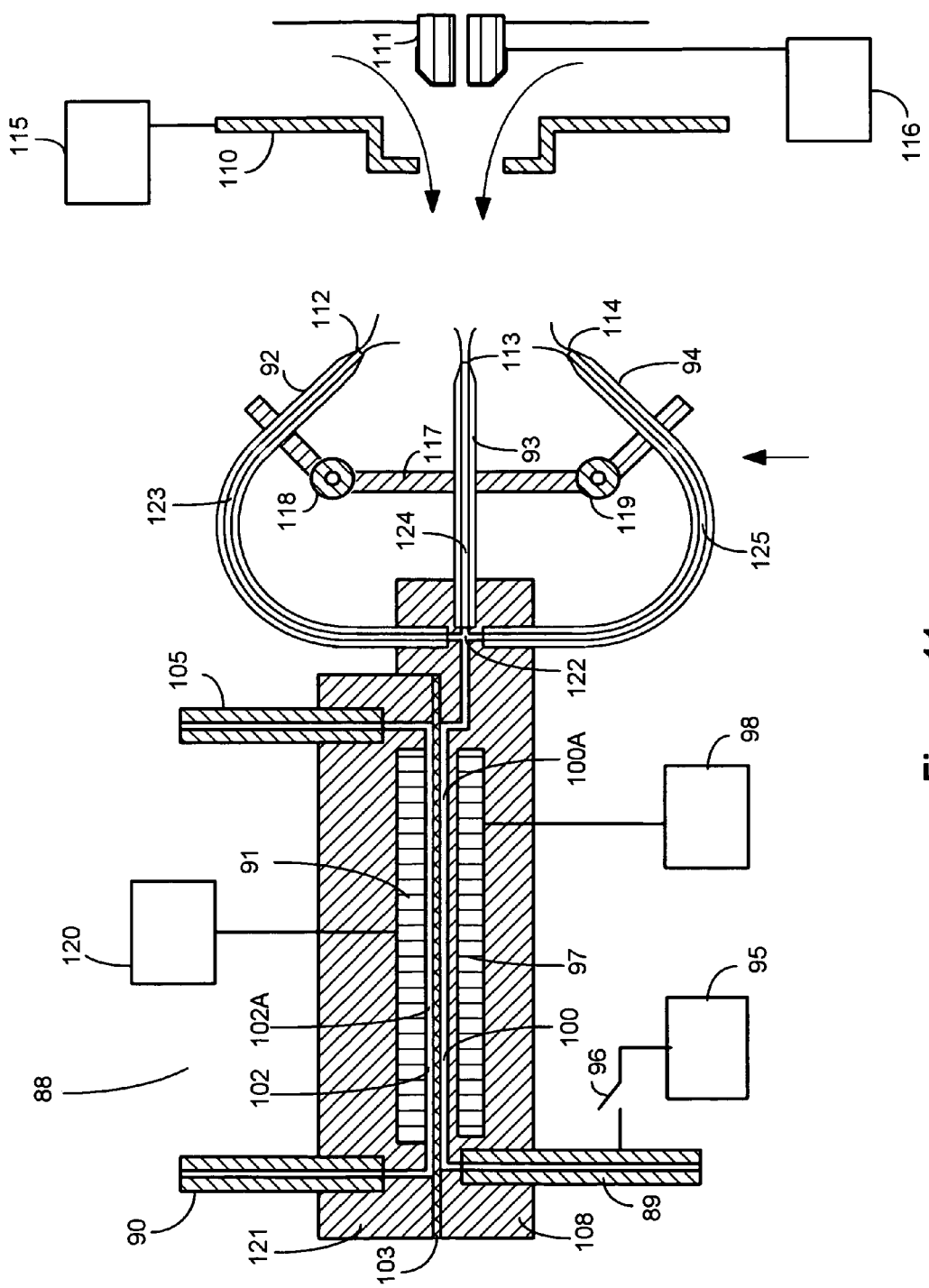
FIG. 11 is a cross section view of a multiple exit tip charged droplet sprayer assembly comprising first and second solution flow channels separated by a membrane.

An alternative embodiment to the invention is diagramed in FIG. 11 wherein multiple spray tips are connected to flow channel 100 in charged droplet sprayer 88. Solution 100A is introduced into multiple tipped charged droplet sprayer 88 through tube 89 into channel 100. Channel 100 connects to channels 123, 124 and 125 in tubes 92, 93 and 94 respectively through low dead volume junction 122 configured in dielectric body 108. Solution 100A is Electrosprayed simultaneously from tube 92 exit tip 112, tube 93 exit tip 113 and tube 94 exit tip 114 with charged species transferred across membrane 103. Solution or gas 102A enters through tube 105, flows through flow channel 102 and exits through tube 90. Alternatively, solution or gas 102A can enter through tube 90 and exit through tube 105. Solution 102A contacts electrode 91 and dielectric membrane 103 as it flows through channel 102. Semipermeable dielectric membrane 103 serves the same functions as membrane 3 described above. All elements and surfaces configured in first solution 100A flow channel 100 comprise dielectric materials to avoid conducting redox reactions on conductive surfaces in first solution 100A flow pathway 100. Alternatively, elements such as tubes 92, 93, 94 and 89 may comprise conductive materials but are electrically floated during charged droplet spraying to prevent redox reactions from occurring on inside channel surfaces. If tube 89 comprises a conductive material it may be connected or disconnected from power supply 95 using switch 96. Electrical potential is applied to electrode 97 through power supply 98. Electrode 97 is electrically insulated by dielectric body 108 and has no direct contact with solution 100A. Electrode 91, electrically isolated in dielectric body element 121, is configured to be in direct contact with gas or solution 102A flowing through flow channel 102.

Similar to the single tip charge droplet sprayer embodiments shown in FIGS. 1 and 2, the total Electrospray current produced from the multiple tip spray configuration shown in FIG. 11 is a function of the relative electrical potentials applied between electrode 91 and counter electrodes 110 and 111, the compositions of solutions 100A and 102A, the flow rate of solution 100A and the distance between exit tips 112, 113 and 114 and counter electrode 110. Electrodes 91, 110 and 111 are connected to voltage supplies 120, 115 and 116 respectively. Stable single plume or multiple plume Electrosprays can be produced from all exit tips simultaneously when operating charged droplet sprayer 88 shown in FIG. 11. The relative position and angles of exit tips 112, 113 and 114 can be changed by adjusting mounting bracket 117 joints 118 and 119 and by sliding tubes 92, 93 and 94 through mounting bracket 117. Charged droplet sprayer 88 shown in FIG. 11 may be configured and operated with one, two or more than three spray tips. The total charged droplet spray current produced from multiple exit Electrospray tips, operating with single or multiple stable Electrospray plumes formed at each exit tip, can be adjusted by changing the acid, base, salt, buffer or other electrolyte concentration in solution 102A. Total charged droplet Electrospray currents exceeding 1.4 microamps have been achieved with a five spray tip embodiment of charged droplet sprayer 88.

Figure 12:
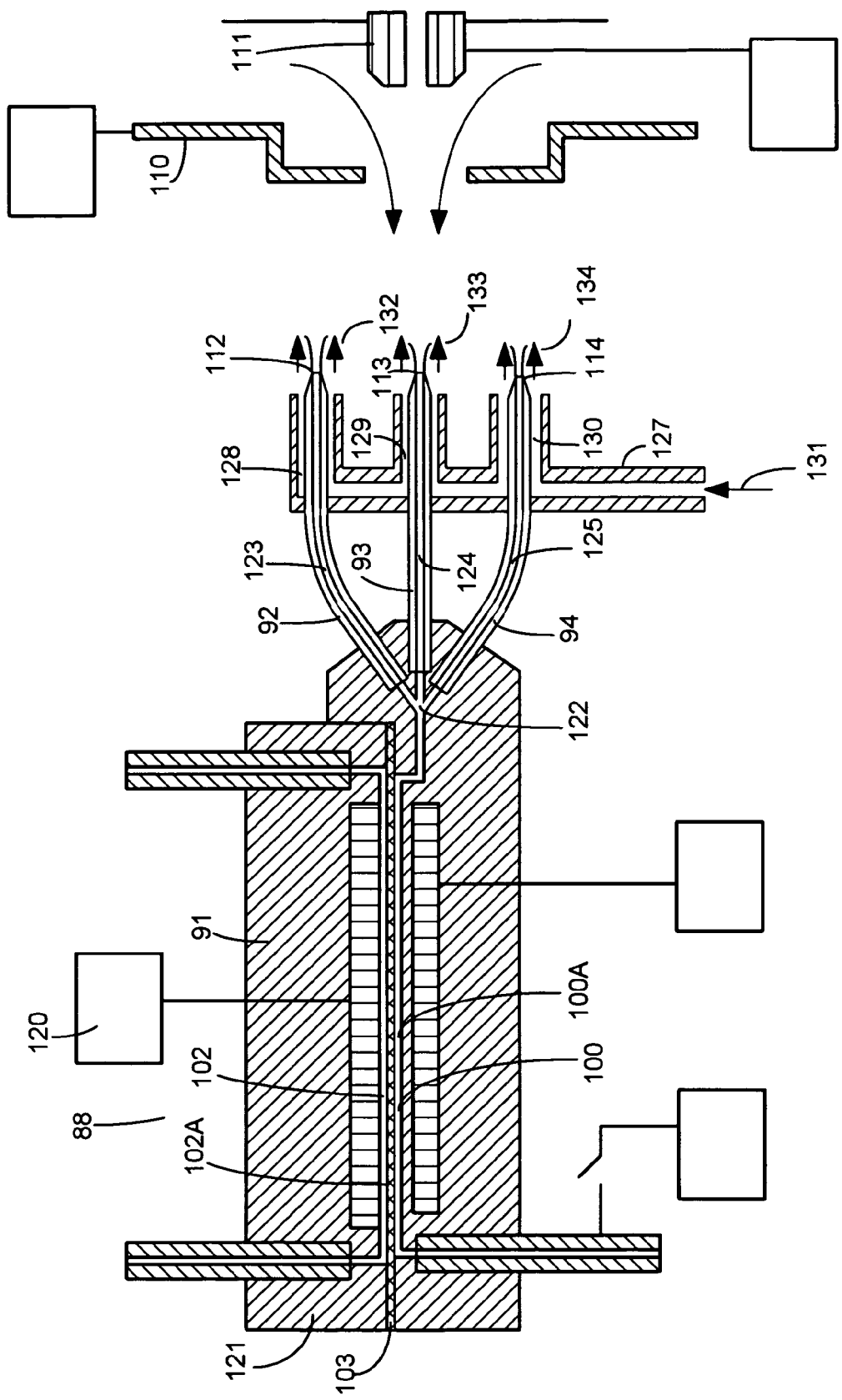
FIG. 12 is a cross section view of a multiple exit tip charged droplet sprayer assembly with pneumatic nebulization comprising first and second solution flow channels separated by a membrane.

An alternative embodiment to the invention is shown in FIG. 12. Pneumatic nebulization is added to multiple spray tip charged droplet sprayer 88. Flow channel 100 connects to flow channels 123, 124 and 125 through low dead volume junction 122 as described above. Tubes 92, 93 and 94 are configured with pneumatic nebulizer gas flow assembly 127 to form gas flow annuli 128, 129 and 130 around tubes 92, 93 and 94 respectively. Nebulization gas 131 enters nebulizer gas flow assembly 127 and exits at outlets 132, 133 and 134 providing gas nebulization shear forces to aid charge droplet formation at exit tips 112, 113 and 114 respectively. Nebulization gas 131 flow rate can be adjusted to optimize charged droplet production performance for different solution 101A compositions or flow rates. Nebulizer gas flow assembly 127 may comprise a dielectric or conductive material. When nebulizer gas flow assembly 127 comprises a dielectric material, the electric field lines passing through such material will wrap more tightly around exit tips 112, 113 and 114 creating a higher electric field at exit tips 112, 113 and 114 during Electrospraying. This effective decrease in the exit tip radius of curvature results in a higher local electric field at exit tips 112, 113 and 114 for a given relative voltage applied to electrodes 91 and counter electrodes 110 and 111. Higher local fields maintained at exit tips 112, 113 and 114 below the onset corona discharge provide more efficient charging of droplets during charged droplet spraying. Pneumatic nebulization assembly 127 may comprise independently adjustable positioning of spray tips 112, 113 and 114.

Multiple second solutions can be separated from a first solution as shown in an alternative embodiment of the invention diagrammed in FIG. 13. Charged droplet sprayer 140 comprises dielectric body 144 and three flow channels 141, 142 and 143. Flow channel 141 is separated from flow channel 142 by semipermeable dielectric membrane 145 and from channel 143 by dielectric membrane 147. Solution or gas 142A flowing through channel 142 contacts membrane 145 and electrode 150 connected to power supply 151. Solution or gas 142A enters and exits flow channel 142 through tubes 152 and 153. Solution or gas 143A flowing through channel 143 contacts membrane 147 and electrode 154 connected to power supply 155. Solution or gas 143A enters and exits flow channel 143 through tubes 156 and 157. Sample solution 141A enters channel 141 through tube 148 and exits through channel 158 of tube 159, forming charged droplet spray 160 from exit tip 161. Charged droplet formation can be aided by nebulizer gas 162 flowing through tube 163 and annulus 164 bounded by the inner diameter of tube 165 and the outer diameter of tube 159. Nebulizer gas 162 exits at annulus 164 exit 167 surrounding exit tip 161. Similar to a two solution charged droplet sprayer as shown in FIGS. 1 and 2, the three solution embodiment provides charged species transfer through both semipermeable membranes 145 and 147 separating solution 141A from solutions or gas 142A and 143A respectively. Charged species transferring through membranes 145 and 147 during charged droplet spraying are driven by the relative voltages applied between electrodes 151 and 155 and counter electrodes 168 and 170. Counter electrodes 168 and 170 are connected to power supplies 169 and 171 respectively.

Charged droplet sprayer 140 can be operated with different compositions for solutions or gases 142A and 143A. Semipermeable membranes 145 and 147 may comprise different materials. The compositions of solutions or gases 142A and 143A and semipermeable membranes 145 and 147 can be optimized for different applications and operating modes. For example the composition of solution or gas 142A and the material used for membrane 145 can be optimized for positive polarity charged droplet production. The composition of solution or gas 143A and the composition of membrane 147 can be optimized for negative polarity charged droplet production. Rapid switching between positive and negative polarity droplet production can be achieved by applying the appropriate voltages to electrodes 151 and 155 and counter electrodes 168 and 170. Relative electrical potentials can be applied between electrodes 151 and 155 to increase or decrease the total Electrospray current or to change the relative concentration of different charged species in sample solution 141A during charged droplet spraying. Two different cation species can be transferred into solution 141A through two different membranes 145 and 147 from two different solutions or gas compositions 142A and 143A during positive polarity charged droplet spraying. Alternatively, anions may be removed from sample solution 141A through membrane 145 or 147 during positive polarity Electrospray ionization. Similarly, in negative polarity Electrospray, two different anion species can be transferred into solution 141A through different membrane 145 and 147 compositions.

The composition or concentration of charged species transferred into sample solution 141A can be modified during Electrospraying by changing the relative voltages applied between electrodes 150 and 154 and/or changing the composition of solutions 142A and 143A. For example, increasing the voltage applied to electrode 150 and lowering the voltage applied to electrode 154 during positive polarity charged droplet spraying will increase the rate of cation transfer across membrane 145 while decreasing the rate of cation transfer across membrane 147. The relative amounts or currents of cation or anion species transferred through membranes 145 and 147 can be ramped or scanned by changing the relative voltages applied to electrodes 150 and 154 during charged droplet spraying. Transfer of cations into solution 141A through membrane 145 while simultaneously removing anions from solution 141A through an appropriate anion exchange membrane 147 can be performed during positive polarity charged droplet spraying by applying the appropriate relative electrical potentials to electrodes 151 and 155 and counter electrodes 168 and 170. Removal of anions during positive polarity charged droplet spraying may aid in reducing unwanted species in solution such as non volatile salts that can contaminate an ion source during operation. Relative adjustments to anion and cation exchange across membranes 145 and 147 can be conducted in negative polarity Electrospray by adjusting the relative voltages applied to electrodes 150 and 154 and counter electrodes 168 and 170. Similar to the single membrane probe embodiment, ramping or scanning of charged species composition and concentration in solution 141A can be achieved by ramping the concentration of acids, bases, salts, buffers or other electrolytes in solutions 142A and 143A during Electrospraying. Adjustments to relative voltages applied to electrodes 150 and 154 and ramping the composition of gases or solutions 142A and 143A can be conducted simultaneously during Electrospraying to optimize ES/MS performance. During operation of charged droplet sprayer 140, including ramping of total Electrospray current and/or ramping of charged species composition in solution 141A, no redox reactions occur on conductive surfaces in the flow path of solution 141A.

Figure 14:
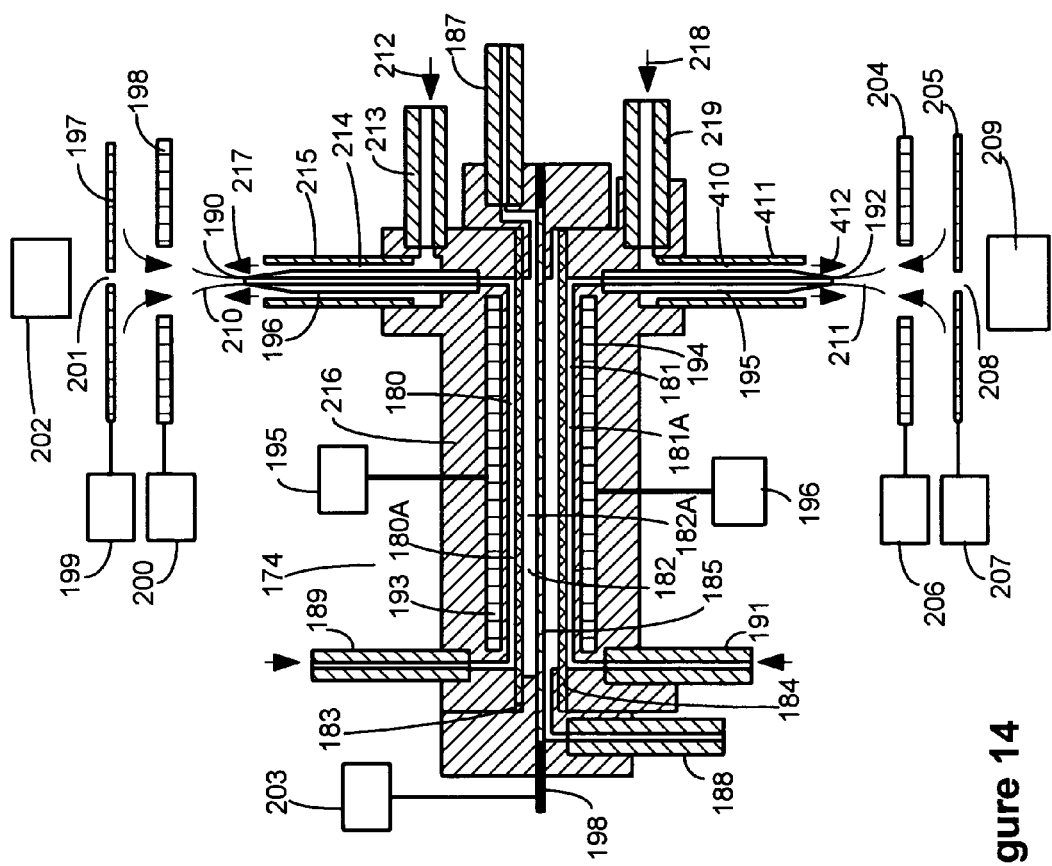
FIG. 14 is a cross section view of a charged droplet sprayer assembly with pneumatic nebulization comprising one second solution flow channel separated from two sample solution flow channels by two membranes.

A cross section diagram of an alternative embodiment of the charged droplet sprayer is shown in FIG. 14. Charged droplet sprayer assembly 174 comprises two first sample solutions 180A and 181A flowing through flow channels 180 and 181 respectively. Flow channels 180 and 181 are separated from a third flow channel 182 by dielectric semipermeable membranes 183 and 184 respectively. Semipermeable membranes 183 and 184 comprise materials chosen to pass selected cations or anions as described in the above sections. Electrode 185, configured as a porous material in flow channel 182 yet sealed or solid along external or sealing edge 198, allows solution or gas 182A to move through it while passing along channel 182. Solution or gas 182A entering channel 182 through tube 187 moves through porous electrode 185 and exits through tube 188. Alternatively, flow of solution or gas 182A can enter and exit channel 182 in the opposite direction. Solution 180A enters channel 180 through tube 189 and exits through tube 196 at exit tip 190. Solution 181A enters channel 181 through tube 191 and exits through tube 195 exit tip 192. Electrodes 193 and 194, connected to power supplies 195 and 196 respectively, are electrically insulated from flow channels 180 and 181, respectively, by dielectric charged droplet sprayer body 216. The electrical potentials applied counter electrodes 197 and 198, connected to power supplies 199 and 200 respectively and electrode 185 connected to power supply 203 form an electric field at exit tip 190. Similarly, electrical potentials applied to counter electrodes 204 and 205, connected to power supplies 206 and 207 respectively and electrode 185 form an electric field at exit tip 192. The same polarity voltage may be applied to counter electrodes 197, 198, 204 and 205 whereby the same polarity charged droplets are sprayed from exit tips 190 and 192 forming charged droplet sprays 210 and 211, respectively. Alternatively, opposite polarity electrical potentials may be applied to counter electrodes 197 and 198 compared to electrical potentials applied to counter electrodes 204 and 205. In this operating mode, positive and negative polarity charged droplets are sprayed simultaneously from exit tips 190 and 192. Charged droplet sprays 210 and 211 may be formed by Electrospraying from exit tips 190 and 192 respectively, or may be formed using pneumatic nebulization in the presence of an electric field. Nebulizing gas 212 passes through tube 213 and annulus 214, bounded by tubes 215 and 196, exiting at 217 surrounding exit tip 190. Similarly, nebulizing gas 218 passes through tube 219 and annulus 410, bounded by tubes 411 and 195, exiting at 412 surroundng exit tip 192. A portion of the ions generated from evaporating charged droplets Electrosprayed from exit tip 190 pass through orifice 201 into vacuum where they are mass to charge analyzed by mass to charge analyzer 202. Simultaneously, a portion of the ions generated from evaporating charged droplets Electrosprayed from exit tip 192 pass through orifice 208 into vacuum where they are mass to charge analyzed by mass to charge analyzer 209.

Charged droplet sprayer assembly 174 allows simultaneous spraying of opposite polarity charged droplets from two solutions 180A and 181A by applying the appropriate electrical potentials to electrodes 185, 198, 197, 204 and 205 as described above. Flow channels 180 and 181 can be configured so that no connected conductive surfaces are in contact with solutions 180A or 181A during Electrospraying. With no conductive surfaces in contact with solutions 180 and 181, all charge species added to or removed from these solutions during charged droplet spraying, pass through membranes 183 and 184, respectively. Solutions 180A and 181A may comprise the same solution from a common source or different solutions. The electrical potentials applied to electrodes 193 and 194 may be set to modify the current flowing through membranes 183 and 184 respectively, however, the electric field established at Electrospray tips 190 and 192 provide the dominant driving force in determining the total Electrospray current generated at charged droplet sprayer exit tips 190 and 192. The electrical current carried by charged species passing through membranes 183 and 184 and through channels 180 and 181 respectively, can be increased by increasing the concentration of the membrane permeable cations or anions in solution 182A. The same or opposite polarity charged droplets may be sprayed simultaneously from exit tips 190 and 192 by applying the same or opposite polarity electrical potentials but not necessarily the same voltage amplitudes to counter electrode sets 197 with 198 and 204 with 205. The voltage values applied to counter electrode sets 197 with 198 and 204 with 205 relative to the potential applied to electrode 185 can be individually adjusted to optimize charged droplet spray currents, independently, at exit tips 190 and 192. Charged droplet sprays from exit tips 190 and 192 can be turned on or off independently, or operated simultaneously, by applying the appropriate voltages. The relative orientation of exit tips 190 and 192 may be optimized for any given application or instrument geometry. For example, simultaneous positive and negative polarity charged droplet spraying from the same solution allows the simultaneous analysis of positive and negative ions produced from the drying charged droplets by two mass to charge analyzers 202 and 209.

Figure 15:
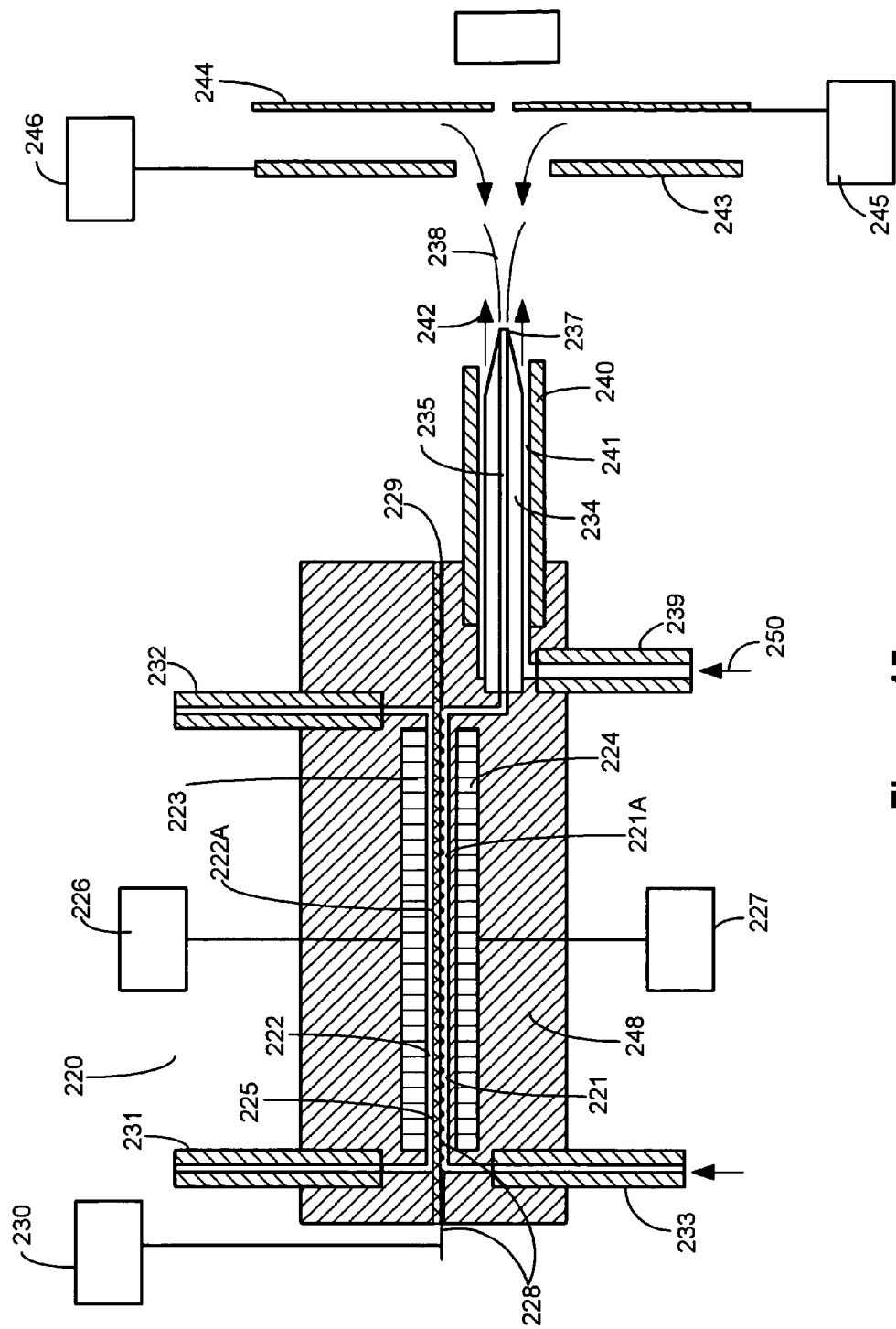
FIG. 15 is a cross section diagram of a charged droplet sprayer assembly with pneumatic nebulization comprising a first and second solution flow channel separated by a membrane and a porous insulated electrode.
Figure 16:
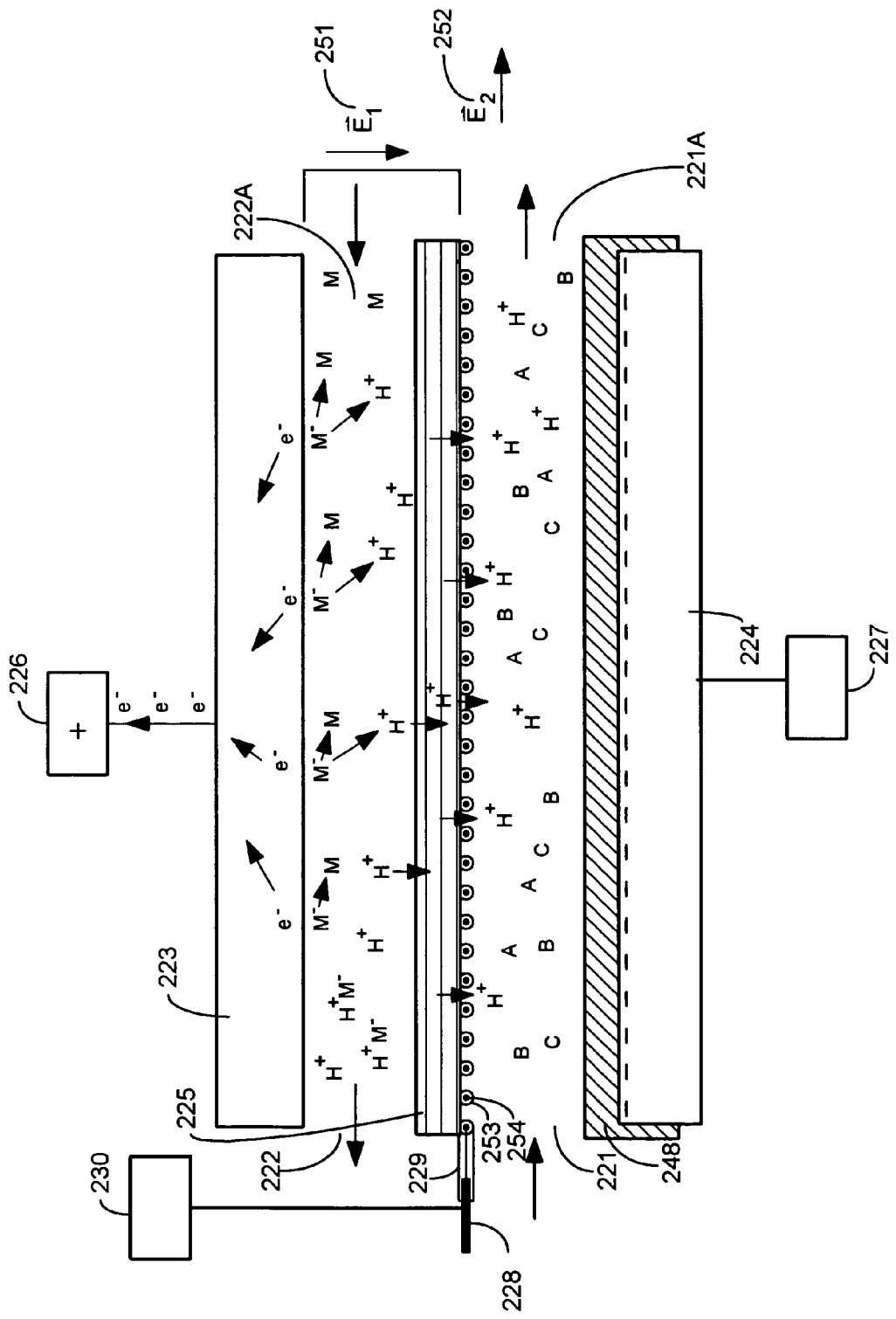
FIG. 16 is a cross section view of the first and second solution flow channels separated by a dielectric membrane and porous insulated electrode.
Figure 17:
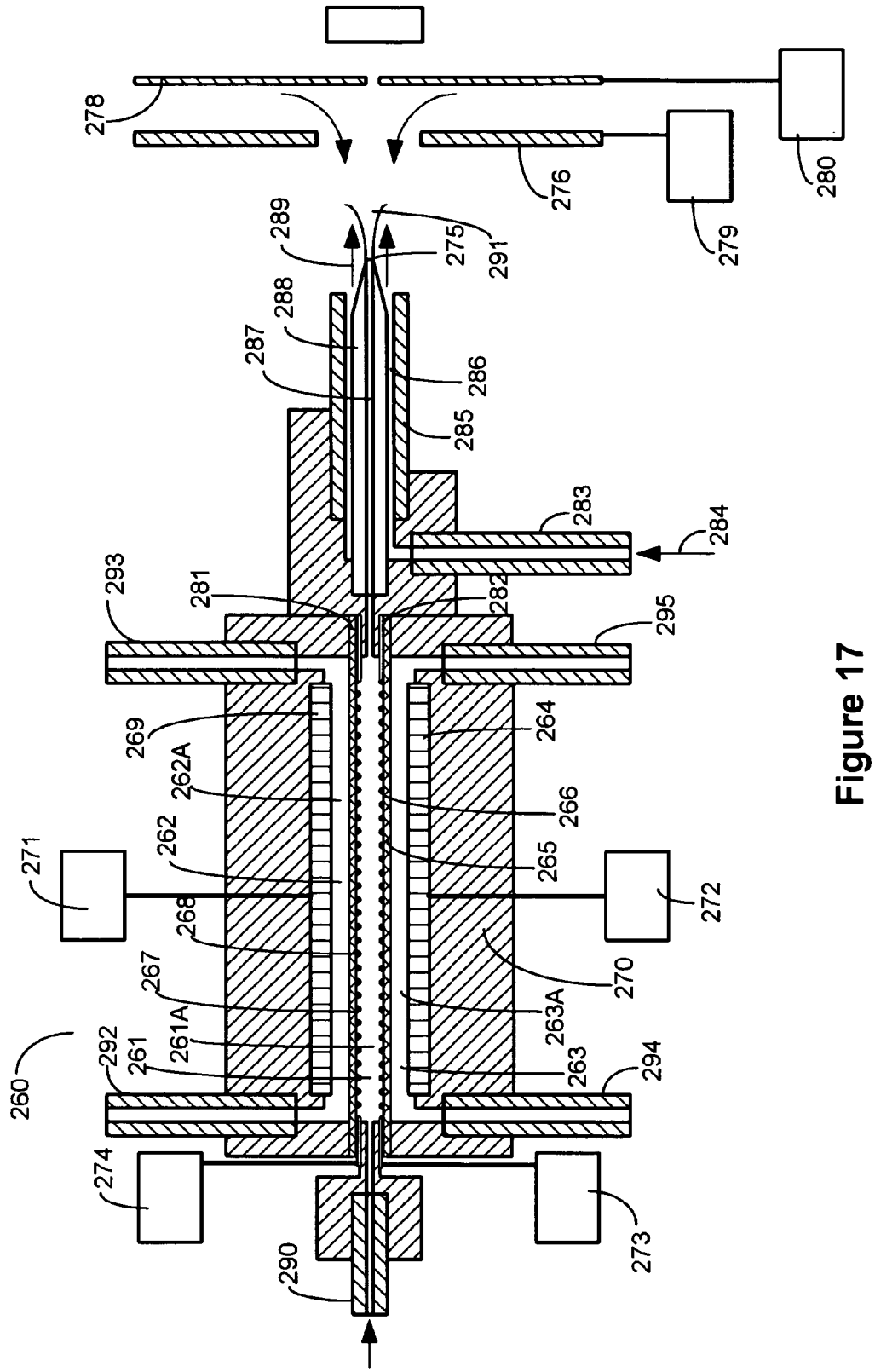
FIG. 17 is cross section view of a charged droplet sprayer with pneumatic nebulization comprising one first solution flow channel separated from two second solution flow channels by two dielectric membranes and two porous insulated electrodes.

The electrical current produced from redox reactions occurring in the second or non sample solution flow channels of the charged droplet sprayer embodiments shown above during charged droplet spraying are determined by the relative electrode and counter electrode potentials and geometries, the composition of the solutions present in the flow channels and the first solution flow rate. Electrical potential applied to the insulated electrodes configured adjacent to the first solution flow channel has a relatively small influence on the droplet spray current produced. A more effective placement of an electrically insulated electrode configured to allow adjustment of the total Electrospray current during operation is shown in FIG. 15. Charged droplet sprayer 220 is configured with sample solution flow channels 221 and second gas or solution flow channel 222 in dielectric body 248. Electrode 223 is in contact with solution 222A in flow channel 222. Electrode 224 is insulated by dielectric body 248 from contact with solution 221A in flow channel 221. Flow channels 221 and 222 are separated by semipermeable dielectric membrane 225 as has been described above. Electrically insulated porous electrode 228 with solid sealing edges 229 is configured in flow channel 221, either flush with the surface of or incorporated into membrane 225. One embodiment of electrode 228 is a porous grid of PTFE (Teflon) coated wire where the PTFE coating is bonded to the surface membrane 225 in contact with solution 221A. The insulating layer surrounding the electrode wire in insulated porous electrode 228 prevents contact between the electrode and solution 221A and prevents the neutralization of charged species being transferred through membrane 225 between flow channels 222 and 221.

Figure 13:
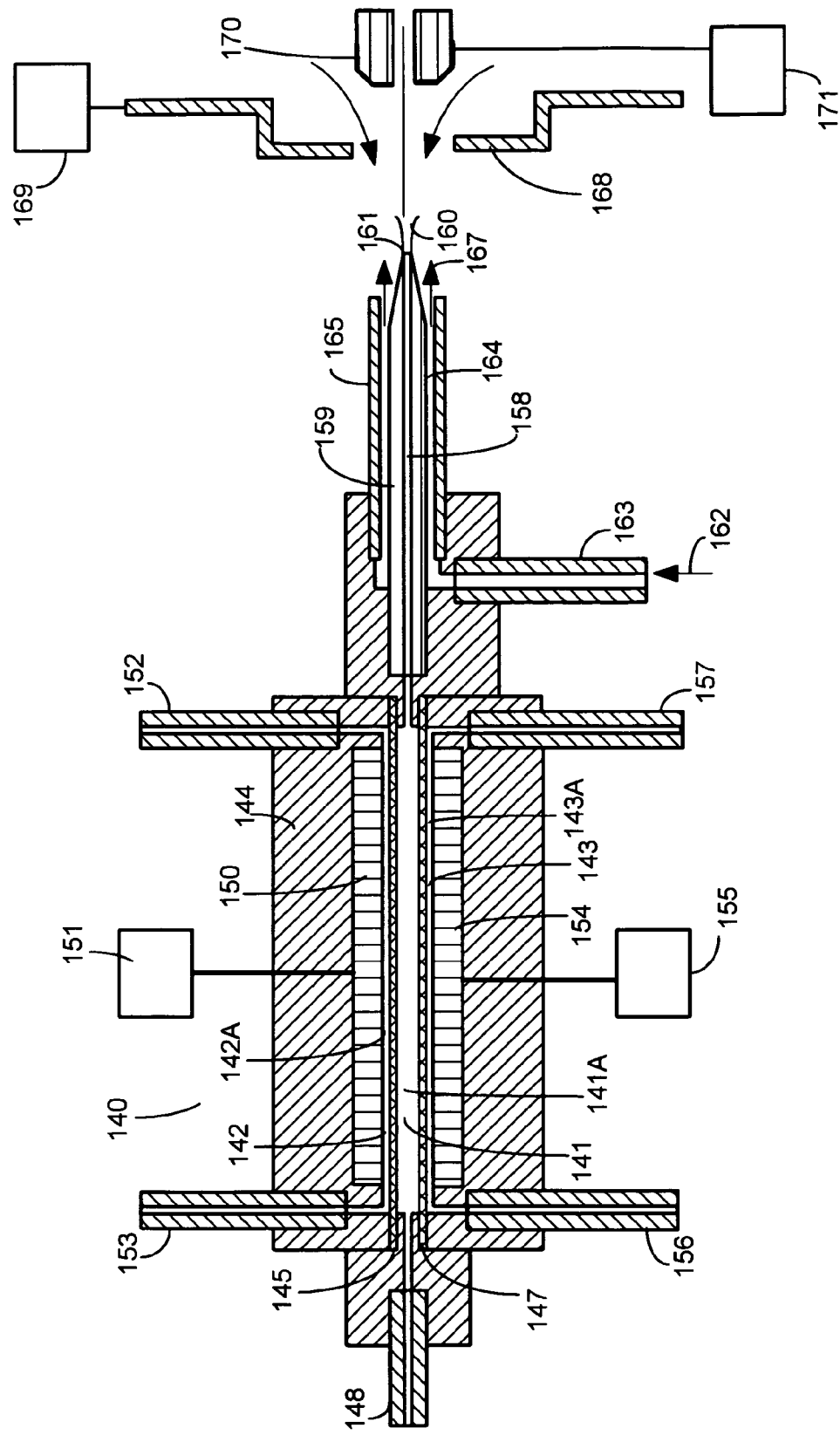
FIG. 13 is a cross section view of a charged droplet sprayer assembly with pneumatic nebulization comprising one first solution flow channel separated from two second solution flow channels by two membranes.

Solution 221A enters through tube 233, flows through channel 221 and channel 235 of tube 234 and exits at exit tip 237 forming charged droplet spray 238. Charged droplets are produced by Electrospraying from exit tip 237 or are formed by pneumatic nebulization in the presence of an electric field as solution 221A leaves exit tip 237. Nebulization gas 250 enters through tube 239 and flows through annulus 241 bounded by tubes 240 and 234 and exits at 242 surrounding exit tip 237. Solution or gas 222A can flow in either direction through channel 222 entering and/or exiting from tubes 231 and 232. Solution 221A is in contact with the insulation of insulated porous electrode 228 and membrane 225 as it flows through channel 221. Electrical potentials are applied to electrodes 223, 228 and 224 through power supplies 226, 230 and 227 respectively. Electrical potentials are applied to counter electrodes 243 and 244 through power supplies 246 and 245 respectively. In the embodiment of charged droplet sprayer 220 shown, no electrically connected conductive surface is in contact with solution 221A during charged droplet spraying. Tube 234 is configured as either dielectric material such as fused silica or is electrically floated or isolated when comprising a conductive material. The thickness and porosity of porous insulated electrode 228 is configured to allow sufficient electric field penetration from channel 221 into membrane 225, to facilitate the transfer of charge from the surface of membrane 225 into flow channel 221. The electric field penetration into membrane 225 from channel 221 does not penetrate significantly into channel 222. The relative potentials applied to insulated porous electrode 228 and electrode 223 can be set to reduce or enhance the electric field present in flow channel 221. Adjustment of the voltage applied to porous insulated electrode 228 serves to modify the electric field formed through solution 221A between electrode 223 and counter electrodes 243 and 224 during charged droplet spraying. The electrical potential applied to electrically insulated electrode 228 can be set to reduce or increase the charged droplet spray current produced for a given solution 221A and solution or gas 222A, electrode geometry, flow rate of solution 221A and relative electrical potentials set on electrodes 223 and 224 and counter electrodes 243 and 244.

The electric field formed between electrode 223 and electrically insulated electrode 228 will influence the electrical current generated at electrode 223 through electrolytic or other redox reactions occurring in flow channel 222. In the embodiment of charged droplet sprayer 220 shown, charge species passing through membrane 225 are transferred into solution 221A through the gaps in porous insulated electrode 228 during charged droplet spraying. FIG. 16 shows a cross section diagram of flow channels 221 and 222. Solution or gas 222A is in contact with electrode 223 and semipermeable dielectric membrane 225 as it flows through channel 222. Solution 221A is in contact with dielectric body 248, dielectric membrane 225, and electrical insulation 253 surrounding conductive elements 254 of electrically insulated porous electrode assembly 228. FIG. 16 shows an example of proton ($H^+$) transfer through membrane 205 from solution 222A into solution 221A during positive polarity Electrospray. In one embodiment of the invention, membrane 225 is configured as Nafion material as described above. The strength of electric field 251 or $E_1$ is determined by the electrical potentials applied between electrode 223 and insulated electrode 228 through power supplies 226 and 230 respectively combined with the electric field 252 or $E_2$ maintained at exit tip 237 by voltages applied to counter electrodes 243 and 244. A voltage drop occurs along flow channels 235 and 221 through solution 221A with electrical field penetration through insulated electrode 228 and semipermeable dielectric membrane 225. The relative electrical potentials applied between electrode 223 and 228 can be set to strengthen or weaken electric field $E_1$ through membrane 225 and across channel 222. H+ ions produced at electrode 223 are transferred through membrane 225 driven initially by electric field $E_1$ and subsequently transferred from membrane 225 into flow channel 221 by the penetration of field 252 or $E_2$ into membrane 225 through the gaps between insulated electrode elements 253 and 254 of electrically insulated electrode assembly 228. Increasing electric field $E_1$ increases the total Electrospray current. The total Electrospray current produced from solution 221A can be rapidly adjusted or scanned during Electrospray ionization by changing or ramping the composition of solution 222A and/or by changing the relative voltages applied to electrode 223 and 228. The embodiment of the invention diagrammed in FIGS. 15 and 16 allows the rapid optimization of charged droplet spray current for a given application with a voltage adjustment applied to electrode 223 for a given solution 221A composition. Electrospray current may be adjusted to optimize performance in the time frame of an eluting liquid chromatography peak. Voltage applied to electrode 223 can be adjusted based on data dependent software feedback during LC/MS operation. A portion of the ions produced from Electrospray 238 pass through the orifice in electrode 244 into vacuum where they are mass to charge analyzed. In alternative embodiments of the invention, electrically insulated porous electrode assembly 228 can be attached to a surface of or incorporated into semipermeable dielectric membrane 225 or positioned between layers of a multiple layer semipermeable membrane 225 configuration.

Increased flexibility in charged droplet spray operation can be achieved by configuring one first solution flow channel separated from two second solution flow channels by two insulated porous electrode assemblies positioned adjacent to two semipermeable dielectric membranes as diagrammed in FIG. 17. First solution 261A enters flow channel 261 through tube 290, traverses flow channel 261 configured in dielectric body 270 and exits through channel 287 in tube 288 at exit tip 275. Second solution 262A entering and exiting flow channel 262 through tubes 292 and 293 contacts electrode 269 and semipermeable dielectric membrane 267. Membrane 267 and insulated porous electrode assembly 268 separate flow channels 262 and 261. Semipermeable dielectric membrane 265 and adjacent insulated porous electrode 266 separate flow channels 263 and 261. Second solution 263A enters and exits flow channel 263 through tubes 294 and 295. Electrode 264 and membrane 265 are in contact with solution 263A as it flows through channel 263. Charged droplet spray 291 is formed from solution 261A at exit tip 275 by unassisted Electrospray or Electrospray with pneumatic nebulization assist. Nebulizing gas 284 flows through tube 283 and annulus 286 bounded by tubes 285 and 288 exiting at 289 surrounding exit tip 275. Charged droplet sprayer 260 is configured such that no redox reactions occur on surfaces in the flow path of first solution 261A. The total Electrospray current is provided by charged species transferred through membranes 267 and/or 265 either into or out of solution 261A during charged droplet spraying. The charged droplet spray current depends on the relative potentials applied to electrodes 269, 264, 268 and 266 through power supplies 271, 272, 274 and 273, respectively and applied to counter electrodes 276 and 278 through power supplies 279 and 280, respectively.

As is the case with the two flow channel charged droplet sprayer embodiment shown in FIG. 15 and described above, the current of charged species passing through semipermeable dielectric membrane 267 in charged droplet sprayer 260 can be adjusted by changing the relative electrical potentials applied between electrode 269 and electrically insulated porous electrode 268. Similarly, the current of charged species passing through semipermeable dielectric membrane 265 can be adjusted by changing the relative electrical potentials applied between electrode 264 and electrically insulated porous electrode 266. Charged droplet sprayer assembly 260 comprising three flow channels provides additional flexibility in optimizing charged droplet production for specific applications. The flexibility in operating modes described for three flow channel charge droplet sprayer 140 diagrammed in FIG. 13 applies to the operation of charged droplet sprayer 260. The addition of two electrically insulated porous electrode assemblies 268 and 266 configured in flow channel 261 adjacent to semipermeable membranes 267 and 266 respectively allows the adjustment of electrical current carried by charged species transferred through membranes 267 and 266. This compliments control of the Electrospray charged droplet production process provided by changing the composition of solutions 262A or 263A. Adjustment of charged droplet spray 291 total Electrospray current can be achieved during Electrospray ionization by changing electrical potentials applied to insulated porous electrode assemblies 266 and 268 configured in charged droplet sprayer 260.

Conventional Electrospray probes configured with conductive surfaces in the sample solution flow path may deposit species on the sample solution flow channel conductive surfaces due to redox reactions during Electrospray ionization. The species that deposit on conductive surfaces due to redox reactions in one ion polarity Electrospray operating mode may deplate and reenter the sample solution through the reverse redox reaction in the reverse ion polarity Electrospray operating mode. The redesolved species reentering the sample solution when the Electrospray polarity is reversed can produce unwanted contamination or interference peaks in the acquired mass spectrum or can modify the true analyte signal due to charge competition or reactions in solution. The embodiments of the invention described above add or remove charge species from the first solution flow through semipermeable membranes, minimizing or preventing deposition of material occurring on conductive surfaces in the first or sample solution flow path. The embodiments of the invention described also provide a means to control the charged droplet spray current for the same sample solution to optimize charged droplet spraying for on line LC/MS or offline analytical applications. The charged droplet sprayers configured according to the invention may also be interfaced to ion mobility separation devices including but not limited to High Field Asymmetric Waveform Ion Mobility Spectrometry (FAIMS) configured in atmospheric pressure ion source assemblies.

Figure 18:
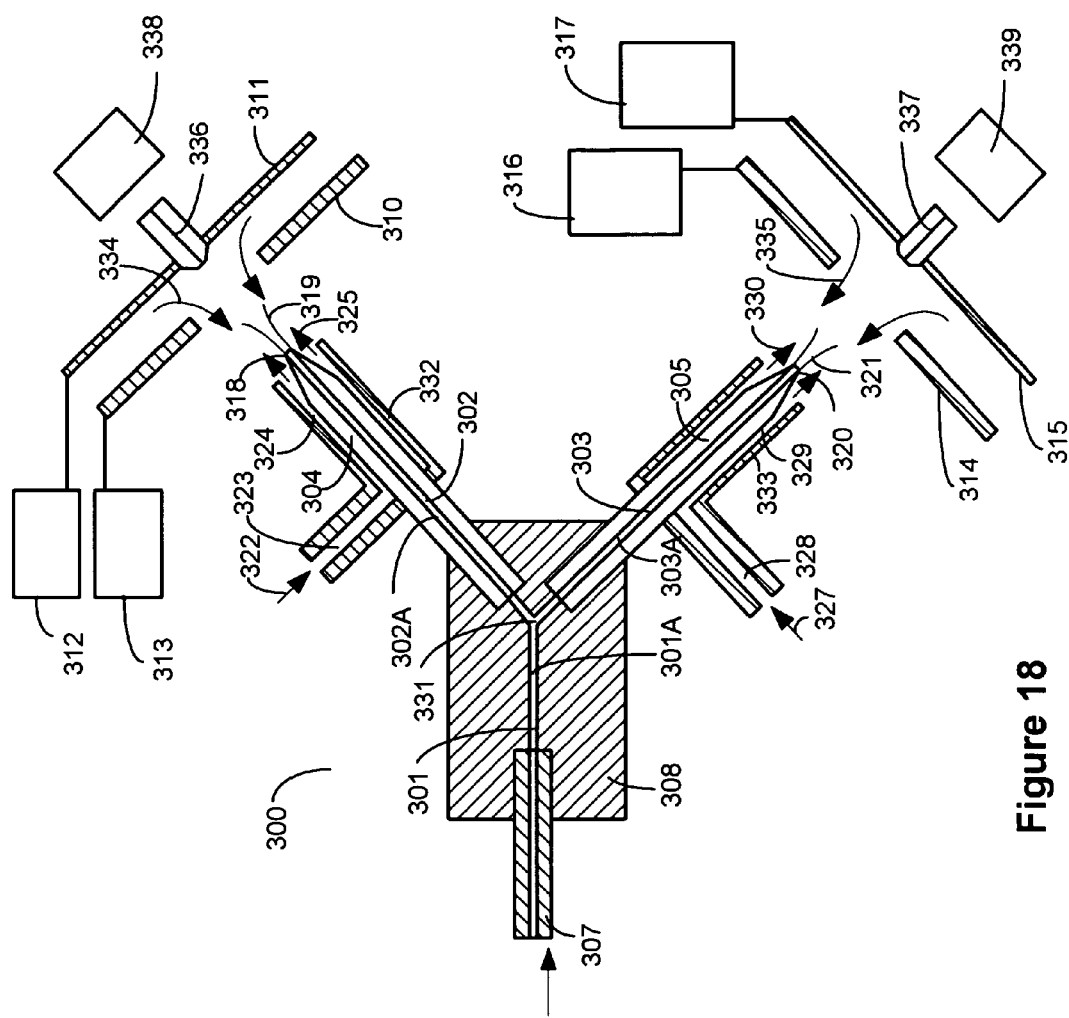
FIG. 18 is a cross section diagram of a charged droplet sprayer with pneumatic nebulization configured to simultaneously spray positive and negative polarity charged droplets from two sprayer tips.

An alternative embodiment to the invention, diagrammed in FIG. 18, provides means for separation of charge in the first solution during charged droplet spraying while avoiding redox reactions occurring on conductive surfaces in the first solution flow path. Limited control of the total charged droplet spray current can be achieved using charged droplet sprayer 300 shown in FIG. 18 without modifying the composition of first solution 301A. Anions and cations present in first solution 301A separate into two solution flow paths during simultaneous positive and negative charged droplet spraying. Dual exit charged droplet sprayer 300 comprises dielectric body 308 with first flow channel 301. Solution 301A enters flow channel 301 through tube 307 and bifurcates through junction 331 into flow channels 302 and 303. Solution 303A flowing through channel 303 in tube 305 exits at exit tip 320 forming charged droplet spray 321. Solution 302A flowing through channel 302 in tube 304 exits at exit tip 318 forming charged droplet spray 319. Electrical potentials are applied to counter electrodes 314 and 315 connected to power supplies 316 and 317, respectively. Electrical potentials are applied to counter electrodes 310 and 311 connected to power supplies 313 and 312, respectively. The electrical potentials applied to electrodes 314 and 315 relative to the electrical potentials applied to electrodes 310 and 311 are set at an amplitude sufficient to maintain opposite polarity Electrospray from exit tips 320 and 318. No connected conductive surfaces are configured in the first solution flow path in charged droplet sprayer 300 minimizing the occurrence of redox reactions on such surfaces during charged droplet spraying. Tubes 304 and 305 may be configured as dielectric material such as fused silica or PEEK or may comprise conductive material such as stainless steel but are electrically floated through connection to dielectric body 308. Depending on the relative electrical polarity applied, counter electrodes 310 and 311 may either provide or accept electrons complimented by the acceptance or providing of electrons by counter electrodes 314 and 315 to complete the electrical circuit during simultaneous opposite polarity charged droplet spraying.

For example, when −3,000 volts (V) is applied to counter electrode 310, −3,500 V applied to capillary entrance and counter electrode 311, +3,000 V applied to counter electrode 314 and +3,500 V applied to capillary entrance and counter electrode 315, positive polarity charged droplet spray 319 occurs at exit tip 318 and negative polarity charged droplet spray 321 occurs at exit tip 320. In this example, electrons are supplied through counter electrodes 310 and 311 and are deposited or accepted on counter electrodes 314 and 315 to complete the electrical circuit. With positive voltages applied to counter electrodes 310 and 311 and equal voltage amplitudes of opposite polarity applied to counter electrodes 314 and 315, the electric field in flow channel 301 is near ground potential. The relative voltages applied to counter electrodes 310 with 311 and 314 with 315 can be adjusted to provide a neutral electric field relative to ground potential in flow channel 301 to minimize the occurrence of redox reactions on the surfaces of upstream flow channel conductive elements. This operating mode allows tube 307 to be connected to a grounded pump or fluid reservoir with no electrical potential present in solution 301A to cause redox reactions at any grounded conductive pump, transfer line or fluid reservoir surface. Alternatively, electrodes 310 and 311 can be operated near ground potential with +6,000 V and +6,500 V applied to electrodes 314 and 315 respectively to achieve positive polarity charged droplet spray 319 from exit tip 318. In the former case with approximately equal but opposite polarity electrical potential applied to the counter electrodes sets the electrical potential of the first solution in channel 301 is effectively ground or zero volts. In the latter operating mode, the relative potential of solution 301A is approximately +3000V. In this case a connection to a grounded LC pump through tube 307 may result in redox reactions on conductive grounded pump surfaces in contact with solution 301A. Such redox reactions can be reduced by configuring a highly resistive flow such as a fused silica packed LC column path between the LC pump and flow channel 301.

Charged droplet sprayer 300 can be operated with unassisted Electrospray or Electrospray with pneumatic nebulization assist at exit tips 318 and 320. Nebulization gas 322 enters channel 323, passes through annulus 324 bounded by tubes 304 and 332 exiting at 325 surrounding exit tip 318. Similarly, nebulization gas 327 enters channel 328, passes through annulus 329 bounded by tubes 305 and 333 exiting at 330 surrounding exit tip 320. Pneumatic nebulization can be turned on or off selectively for one or both spray tips during charged droplet spraying. The relative liquid flow rates through channels 302 and 303 can be adjusted by applying different forces such as nebulization gas flow differentially at exit tips 318 and 320 or modifying the length or inner diameter of tubes 304 and 305. During simultaneous positive and negative charged droplet spraying, solutions 302A and 303A have a net charge of opposite polarity. Anion and cation species are deposited on counter electrode spray surfaces or swept into respective capillary orifices during charged droplet spraying. Anions and cations are not deposited on charged droplet sprayer 300 internal flow channel surfaces through redox reactions during simultaneous spraying of positive and negative polarity charged droplets. Positive and negative polarity ions are produced simultaneously from evaporating charged droplet sprays 319 and 321 moving against counter current drying gas flows 334 and 335 respectively. A portion of the ion population produced is swept through capillary bores 336 and 337 into vacuum where positive and negative ions are mass to charge analyzed with a single or separate mass to charge analyzers 338 and 339 respectively.

The embodiment of the invention as shown in FIG. 18 can be simplified, while retaining performance features and increasing control of the charged droplet spray process, if simultaneous positive and negative charged droplet production is not required. A diagram of an alternative embodiment of the invention is shown in FIGS. 19A, 19B and 19C. Counter electrodes 314 and 315 as diagrammed in FIG. 18 are replaced by repositioned counter electrode 341 connected to power supply 342. Countercurrent electrode 341 is positioned relative to exit tip 320 such that solution 303A flowing through channel 303 of dielectric tube 305 exits at exit tip 320 making contact with counter electrode 341 through liquid connection 340 as shown in FIG. 19B. During charged droplet spraying from exit tip 318, electrical current flows to counter electrode 341 and power supply 342 through the liquid connection 340. When operating charged droplet sprayer 348, the electrical circuit formed between power supplies 312 and 313 and power supply 342 is completed through charged droplet spray 319 from solution 302A directed to counter electrodes 310 and 311 and through liquid connection 340 maintained between solution 303A and counter electrode 341.

Liquid connection 341 eliminates the need to optimize and balance two opposite polarity sprays simultaneously and provides a more refined control of the electric field applied at exit tip 320. Anions or cations neutralized on electrode 341 can be readily washed off as required, even during charged droplet spraying, or retained for additional analysis. Electrode 341 can be moved during charged droplet spraying to spatially separate species deposited at different times during $MS^n$ or $LC/MS^n$ analysis. Such deposited species can be reanalyzed subsequent to the analysis in which deposition occurred. When positive polarity charged droplet spraying of solution 301A containing nonvolatile salts is conducted, anions of the nonvolatile salts are deposited on electrode 341 during spraying. This deposition of nonvolatile species reduces the amount of contamination species deposited on counter electrodes 310 and 311 from positive charged droplet spray 319. Although solution 301A is split into 2 flows 302A and 303A flowing through channels 302 and 303 respectively, a large percentage of positive ions of interest will be directed to the positive spray flow channel minimizing positive ion signal loss in mass to charged analysis during positive polarity charged droplet spraying. Similarly, during negative polarity charged droplet spraying, negative ions in solution will be directed into the negative polarity flow path minimizing any reduction of negative ion signal in mass to charge analysis. The flow rate of solution 303A through flow channel 303 can be minimized by reducing the diameter of channel 303 or increasing its length while minimizing the effect on electrical current. Electrospray operation with no flow through channel 303 can be achieved with the alternative embodiment of the invention diagrammed in FIG. 19C. Charged droplet sprayer 348 dielectric tube 305 and channel 303 is shown as dielectric tube 343 and channel 347 respectively in FIG. 19C. Power supply 342 connects to solution 303A through the conductive surface 345 of electrode 344. Electrical current flows through electrode 344 to power supply 342 during Electrospraying with redox reactions occurring on conductive surface 345 displaced from the solution flow path 302. In the embodiment shown in FIG. 19C, all sample solution flow traverses flow channel 302 with only charged species moving through channel 347 to electrode 344 during Electrospraying. Electrode 344 can be removed and cleaned to prevent carryover of contamination species when switching polarity in Electrospray ionization. Alternatively, rapid deplating of contamination species can be achieved from surface 345 when switching polarity in charged droplet spray compared with conventional Electrospray probe geometries, reducing the flushing time between opposite polarity Electrospray MS analysis.

Dual output charged droplet sprayers as diagrammed in FIGS. 18 and 19 can be configured with semipermeable dielectric charge transfer membranes as described for FIGS. 1 through 17 above. The combined configuration of both charged droplet sprayer embodiments shown in FIGS. 1 and 18 or 19 provides the operation and performance advantages and improvements of both individual charged droplet sprayer embodiments. An alternative embodiment to a combined charged droplet sprayer comprises the introduction of first and second solutions into a common flow channel without separation by a semipermeable membrane is diagrammed in FIG. 20. Similar to the dual polarity charged droplet sprayer embodiment diagrammed in FIG. 18, charged droplet sprayer 350 with dielectric body 370 comprises opposite polarity Electrospray or pneumatic nebulization charged droplet sprayers. Positive and negative polarity charged droplets are simultaneously sprayed from exit tips 360 and 361 during operation. Alternatively, exit tip 360 may be configured with a repositioned counter electrode 363 to form a liquid connection with solution 357A flowing through channel 357 of dielectric tube 359 similar to liquid connection 340 shown in FIG. 19. First or sample solution 353A is introduced into flow channel 351 through tube 354 and channel 353. Second solution 352A is introduced into flow channel 351 through tube 355 and channel 352. Solutions 352A and 353A may mix or may have minimum mixing while flowing through channel 351 depending on relative concentrations of solution components, relative flow rates, and the influence of the electric field applied through flow channels 356 and 357. The introduction of solution 352A allows the addition of chemical species required to optimize the performance of the opposite polarity charged droplet sprays for component sample species in solution 353A for in a given $ES/MS^n$ analytical application. For example, cations may be added through an acid containing solution 352A to an aqueous first solution 353A in flow channel 351 during positive polarity charged droplet spraying from exit tip 361. Charge separation occurs in mixed or layered solution 351A as solution 351A flow bifurcates into flow channels 356 and 357.

As an example of one operating mode, consider positive polarity charged droplet spraying from exit tip 361 and negative polarity charged droplet spraying from exit tip 360. Positive electrical potentials applied to counter electrodes 363 and 364 through power supplies 366 and 365 respectively are of equal amplitude but opposite polarity from the negative electrical potentials applied to counter electrodes 367 and 368 through power supplies 369 and 370 respectively. No connected conductive surfaces are present in the solution flow paths of charged droplet sprayer 350 so redox reactions occurring on flow channel surfaces during charged droplet spraying are minimized. Positive charged species in solution 351A will move into channel 356 and negative charged species will move into channel 357 during charged droplet spraying. The embodiment of the invention diagrammed in FIG. 20 allows the introduction of desired chemical species into the first solution flow and provides separation of charged species in solution of opposite polarity prior to spraying. Variables such as second solution composition and flow rate and relative electrical potentials applied to counter electrodes can be adjusted to optimize charge droplet spraying performance for specific applications. Operation with pneumatic nebulization of charged liquid droplets from Electrospray tips 360 and 361 is achieved by turning on nebulization gas flows 363 and 362 respectively In an alternative embodiment of the invention, diagrammed in FIG. 21, the mixing of a sample solution with a second solution is minimized while retaining the ability to add charged species to or remove charge species from the first solution flow during charged droplet spraying. Charged droplet sprayer 380 comprises dielectric body 408 and two solution inlets and two outlets. First sample solution 381A enters through channel 381 in tube 384 and passes through junction 387 becoming solution 389A. Solution 389A passes through channel 389 in tube 388, exiting at exit tip 390 forming charged droplet spray 407. Second solution 383A enters through tube 383, passes through channel 382 and bifurcates into flow channels 386 and 385. Flow channel 385 connects with flow channel 392 in tube 391. Solution 392A passing through flow channel 392 exits at exit tip 393 making electrical contact through liquid connection 394 to counter electrode 395 connected to power supply 396. Counter electrodes 397 and 398 are connected to power supplies 399 and 400 respectively. Charged species generated in unassisted Electrospray or Electrospray with pneumatic nebulization assist plume 407 impinging on counter electrodes 397 and 398 and passing through capillary bore 406 complete the electrical circuit with counter electrode 395 through liquid connection 394 as has been previously described for charged droplet sprayer 348 diagrammed in FIG. 19. Separation of charged species in solutions 381A and/or 382A occurs at junction 387 or in flow channel 382 with opposite polarity charge passing into flow channels 386 and 385. The flow rate of solution 383A and the flow resistance of channel 392 can be adjusted to determine the net flow and direction of flow of solution 386A in channel 386. Alternatively, the electrical contact with solution 392A can be made with a zero flow junction as diagrammed in FIG. 19C. During operation of this embodiment, the flow rate and direction of flow through channel 386 matches the flow rate and direction of flow of second solution 383A.

When spraying positive polarity charged droplets from exit tip 390, positive charge species can move with solution 386A flow through channel 386 adding to first solution 381A at junction 387. Alternatively, during positive polarity charged droplet spraying, negative ion species separating from positive polarity ion species in solution 381A move from solution 381A into channel 386 at junction 387. The movement of negative charge species into flow channel 386 can occur with net solution flow in either direction in flow channel 386. Similarly, when spraying negative polarity charge droplets from exit tip 390, negative charged species can be added to solution 381A at junction 387 or positive charged species can be removed from solution 381A at junction 387. For either positive or negative polarity charged droplet spraying, the flow rate and direction of solution flow through channel 386 can be controlled by the adjusting the flow rate and direction of flow of solution 383A in channel 382 for a given flow channel 385 and 392 geometry. The geometry of channels 386 and 385 can be modified to optimize solution flow and charged species movement into or out of first solution 381A. For example, channel 386 and 385 can be configured as a single straight channel with a tee into channel 382 minimizing channel length to reduce dead volume and solution electrical and fluid flow resistance. Solution 389A can be Electrosprayed from exit tip 390 with or without pneumatic nebulization assist. Nebulizer gas 401 flowing through channel 402 and annulus 403 bounded by tubes 404 and 388 exits at 405 surrounding exit tip 390. Electrical potentials applied to counter electrodes 397 and 398 through power supplies 399 and 400 respectively form an electric field at exit tip 390. The electrical potential applied to counter electrode 395 through power supply 396 contacts solution 392A through liquid connection 394. The occurrence of redox reactions on dielectric or electrically isolated flow channel surfaces in charged droplet sprayer assembly 380 is minimized during charged droplet spraying. Total charged droplet spray current leaving exit tip 390 is matched by electrical current flowing through exit tip 393 and through liquid connection 394 to electrode 395. The field strength at exit tip 390, solution compositions and flow rates, flow channel geometries and the voltage applied to counter electrode 395 relative to counter electrodes 397 and 398 will determine the total charged droplet spray current leaving exit tip 390. Flow rates and the composition of solutions 381A and 383A, the voltages applied to electrodes 395, 387 and 398 and nebulization gas 401 flow rate can be adjusted to optimize charged droplet spray 407 for a given application. A portion of the ions produced from evaporating charged droplet spray 407 are directed through capillary orifice 406 into vacuum where they are mass to analyzed by mass to charge analyzer 408.

Although flow channels, tubes, junctions and annulus regions are shown in diagrams configured as both integrated and discrete elements, these structures and elements can be configured in fully integrated devices and microfabricated devices to minimize dead volume and to optimize flow channel geometry. The charged droplet sprayer embodiments of the invention described above or combinations of such embodiments, produce charged droplet spray currents where all or a portion of such spray current is generated by redox reactions occurring on surfaces external to the first solution flow path. The total Electrospray current can be adjusted using embodiments of the invention without modifying the input composition of the first solution. Small diameter channels can be configured to supply charged species in nanospray devices for first solution flow rates less than 1 ul/min. Calibration components or reactants can be added to first solution flows from second solutions through specifically configured selective membranes or flow junctions. Combinations of the embodiments shown in FIGS. 1 through 21 above can be configured to utilize the control and performance advantages of each charged droplet sprayer embodiment. The charged droplet sprayer embodiments described herein can be configured and operated to optimize performance for applications ranging from ion sources in mass spectrometers to aerosol generators to painting. Alternative geometries of the embodiments diagrammed can be configured with variations on the elements described herein. Using the embodiments of the inventions or combinations of embodiments of charged droplet sprayer devices configured according to the invention, charged droplet spraying may be conducted whereby the total charged droplet spray current generated is greater than the electrical current occurring due to redox reactions on conductive surfaces in the first solution flow channel. The ratio of the total charged droplet spray current generated from redox reactions occurring on surfaces external to versus internal to the first solution flow path can be adjusted using embodiments or combinations of embodiments of the invention. Ultrasonic nebulization, alternative configurations of pneumatic nebulizers or alternative configurations of counter electrodes can be incorporated as alternative embodiments of the invention.

The invention can be operated to conduct conductivity or pH scans by changing composition of the second solution, changing the flow rate of the first solution for a given second solution composition or changing the relative potentials applied to selected electrodes as described above. Conductivity or pH scanning can be conducted during Electrospray ionization with or without a semipermeable membrane separating the sample solution and second solution. Rapid pH or conductivity scanning can be conduced during the elution time of a liquid chromatography peak through preprogrammed or data dependent control. Scanning pH allows the optimization of ion signal for sample molecules that have different pI values in a sample solution. Multiple membrane interfaces between sample solutions and second solutions can be configured according to the invention in parallel or in a serial arrangement in the sample solution flow paths. Membranes of different thickness and compositions and layers of membranes comprising the same or different materials can be configured in charged droplet sprayers configured and operated according to the invention.

Although the present invention has been described in accordance with the embodiments shown, one of ordinary skill in the art will recognize that there can be variations to the embodiments and such variations would fall within the spirit and scope of the present invention.

We claim:

1. An apparatus for producing charged droplets comprising:
   a. a first solution flow channel with at least one exit end,.
   b. a first solution in said first solution flow channel,
   c. at least one second solution flow channel,
   d. at least one second solution in said at least one second solution flow channel,
   e. said first and said at least one second solution and said first end said at least one second flow channel are separated by at least one membrane; and
   f. means for producing a charged droplet spray at said exit end of said first solution flow channel whereby at least a portion of the total charged droplet spray current is transferred through said membrane.

2. An apparatus for producing charged droplets comprising:
   a. a first solution flow channel with at least one exit end,
   b. a first solution in said first solution flow channel,
   c. at least one second solution flow channel,
   d. at least one second solution in said at least one second solution flow channel,
   e. said first and said at least one second solution and said first and said at least one second flow channel are separated by at least one membrane;
   f. means for producing a charged droplet spray at said exit end of said first solution flow channel whereby at least a portion of the total charged droplet spray current is transferred through said membrane; and
   g. means for changing the composition of said second solution during said charged droplet production.

3. An apparatus for producing charged droplets comprising:
   a. a first solution flow channel configured with at least one exit end,
   b. a first solution flow in said first solution flow channel
   c. means for generating one electric field at said at least one exit end, and
   d. means for forming a charged droplet spray of said first solution from at least one exit end; and
   e. charged droplet spray producing current which is greater than the current produced from redox reactions occurring on conductive surfaces in said first solution flow channel.

4. An apparatus for producing charged droplets comprising:
   a. a first solution flow channel configured with at least one exit end,
   b. a first solution flow in said first solution flow channel,
   c. means for generating an electric field at said at least one exit end, and
   d. forming a charged droplet spray of said first solution from at least one exit end, with no redox reactions occurring on conductive surfaces in said first solution flow channel.

5. An apparatus as in one of claims 1-4 whereby said first solution flow channel is configured with at least two exit ends.

6. An apparatus according to claim 5 whereby charged droplets of the same polarity are sprayed from at least two of said exit ends.

7. An apparatus according to claim 5 whereby charged droplets of opposite polarity are sprayed from at least two of said exit ends.

8. An apparatus as in one of claims 1-4, further comprising a counter electrode, whereby at said at least one exit ends is positioned such that solution leaving said at least one exit end forms an electrical contact with said counter electrode.

9. An apparatus as in of claims 1-4 whereby an insulated porous electrode is positioned in said first solution flow channel adjacent to said membrane.

10. An apparatus as in one of claims 1-4 wherein said membrane comprises a semipermeable membrane.

11. A method for producing charged droplets comprising:
   a. utilizing an apparatus comprising a first solution flowing through a first solution flow channel with at least one exit end having an electric field present at least one exit end and
   b. spraying charged droplets from said at least one exit end whereby the current produced by said charged droplet spray is greater than the current produced from redox reactions occurring on surfaces in said first solution flow channel.

12. A method for producing charged droplets comprising:
a. utilizing an apparatus comprising a first solution flowing through a first flow channel with at least one exit end having an electric field present at least one exit end and at least one second solution flowing through at least one second flow channel whereby said first and said at least one second solution and said first and said at least one second flow channel are separated by at least one membrane;
b. transferring charged species through said at least one membrane forming a current through said at least one membrane; and
c. spraying charged droplets from said at least one exit tip whereby said charged species current through said at least one membrane comprises at least a portion of said total charged droplet spray current.

13. A method for producing charged droplets according to claim 12, comprising the further step of changing said charged droplet spray current by changing the composition of said second solution.

14. A method for producing charged droplets according to claim 12 or 13, comprising the further step of changing the pH of said first solution during charged droplet spraying by changing the composition of said second solution.

15. A method for producing charged droplets comprising:
a. utilizing an apparatus comprising a first solution and a first solution flow channel with at least one exit end and a second solution and a second solution flow channel, said first and said second solution flow channels forming a junction upstream of said exit end;
b. transferring charged species through said junction forming a current through said junction; and
c. spraying charged droplets from said at least one exit tip whereby said current through said junction comprises at least a portion of said charged droplet spray current.

16. A method for producing charged droplets comprising:
a. utilizing an apparatus comprising a first-solution and a first and second flow channel, said solution flowing in both said flow channels, with each said flow channels comprising exit ends, respectively, wherein said first and second flow channels form a junction upstream of each said exit end, and wherein said exit end of said second channel is positioned such that said solution leaving said second channel exit end makes an electrical contact with an electrode;
b. spraying charged droplets from said exit end of said first flow channel in the presence of an electric field; and
c. adjusting the electrical potential applied to said electrode whereby at least a portion of the charged droplet spray current is supplied from said electrode.

* * * * *